(12) United States Patent
Bhimavarapu et al.

(10) Patent No.: US 10,231,649 B2
(45) Date of Patent: Mar. 19, 2019

(54) SERVICE SCHEDULING AND NOTIFICATION SYSTEMS FOR PATIENT SUPPORT APPARATUSES

(71) Applicant: Stryker Corporation, Kalamazoo, MI (US)

(72) Inventors: Krishna Sandeep Bhimavarapu, Kalamazoo, MI (US); Annie Désaulniers, Kalamazoo, MI (US); Kevin Mark Patmore, Plainwell, MI (US); Thomas Joseph Durlach, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/786,699

(22) Filed: Oct. 18, 2017

(65) Prior Publication Data
US 2018/0110445 A1    Apr. 26, 2018

Related U.S. Application Data

(60) Provisional application No. 62/410,869, filed on Oct. 21, 2016.

(51) Int. Cl.
*G08B 21/00* (2006.01)
*A61B 5/11* (2006.01)
(Continued)

(52) U.S. Cl.
CPC ............ *A61B 5/1115* (2013.01); *A61B 5/002* (2013.01); *A61B 5/0017* (2013.01); *A61G 7/00* (2013.01);
(Continued)

(58) Field of Classification Search
CPC ..... A61B 5/002; A61B 5/0017; A61B 5/1115; G08B 21/043; G08B 21/22
(Continued)

(56) References Cited

U.S. PATENT DOCUMENTS

| 4,665,573 A | 5/1987 | Fiore |
| 5,898,288 A | 4/1999 | Rice et al. |

(Continued)

FOREIGN PATENT DOCUMENTS

| CA | 2393880 A1 | 1/2004 |
| CA | 2529091 A1 | 12/2004 |

(Continued)

*Primary Examiner* — Mark S Rushing
(74) *Attorney, Agent, or Firm* — Warner Norcross + Judd LLP

(57) ABSTRACT

Patient support apparatuses include a frame, support surface, and a controller. The controller provides notification to a user of a service event relating to the patient support apparatus. The controller limits functionality of a component of the patient support apparatus based upon a severity of the service event. The controller may also, or alternatively, detect when a control is activated by a user and, in response to such activation, determine whether the patient support apparatus has been marked for use or marked for servicing. If marked for use, the controller responds in a first manner, and if marked for service, the controller responds in a different manner. In other embodiments, a method is provided for determining an order in which multiple patient support apparatuses should be service. In still other embodiments, the patient support apparatus automatically changes to an unusable configuration when in need of high priority service.

25 Claims, 13 Drawing Sheets

(51) Int. Cl.
  *A61B 5/00* (2006.01)
  *G08B 21/04* (2006.01)
  *A61G 7/00* (2006.01)
  *G08B 21/22* (2006.01)

(52) U.S. Cl.
  CPC ........ *G08B 21/043* (2013.01); *A61G 2203/20* (2013.01); *A61G 2203/70* (2013.01); *G08B 21/22* (2013.01)

(58) Field of Classification Search
  USPC .......................................................... 340/540
  See application file for complete search history.

(56) References Cited

U.S. PATENT DOCUMENTS

| | | | |
|---|---|---|---|
| 6,334,442 B1 | 1/2002 | Altamura | |
| 6,505,368 B1 | 1/2003 | Ellis et al. | |
| 7,065,816 B2 | 6/2006 | McGettigan | |
| 7,690,059 B2 | 4/2010 | Lemire et al. | |
| 7,702,481 B2 | 4/2010 | Dionne et al. | |
| 7,774,215 B2 | 8/2010 | Rosow et al. | |
| 8,011,039 B2 | 9/2011 | Stryker et al. | |
| 8,060,274 B2 | 11/2011 | Boss et al. | |
| 8,121,856 B2 | 2/2012 | Huster et al. | |
| 8,777,879 B2 | 7/2014 | Johnson | |
| 8,914,924 B2 | 12/2014 | Stryker et al. | |
| 9,056,556 B1 | 6/2015 | Hyde et al. | |
| 9,079,505 B1 | 7/2015 | Hyde et al. | |
| 9,123,229 B2 | 9/2015 | Slavin et al. | |
| 9,230,421 B2 | 1/2016 | Reeder | |
| 9,539,156 B2 | 1/2017 | Lemire et al. | |
| 9,713,728 B2 | 7/2017 | Smith | |
| 2004/0172182 A1* | 9/2004 | Pathare | ............ B60K 35/00 701/36 |
| 2005/0113996 A1 | 5/2005 | Pillar et al. | |
| 2006/0136105 A1 | 6/2006 | Larson | |
| 2007/0174964 A1* | 8/2007 | Lemire | ................. A61G 7/005 5/600 |
| 2008/0109964 A1 | 5/2008 | Flocard et al. | |
| 2008/0312971 A2* | 12/2008 | Rosow | ................... G06Q 10/02 705/5 |
| 2009/0088924 A1 | 4/2009 | Coffee et al. | |
| 2011/0208541 A1* | 8/2011 | Wilson | .................. A61G 7/018 705/3 |
| 2011/0301516 A1 | 12/2011 | Lafleche et al. | |
| 2011/0301807 A1 | 12/2011 | Staaf | |
| 2012/0123951 A1 | 5/2012 | Hyatt et al. | |
| 2012/0137436 A1* | 6/2012 | Andrienko | ............ A61G 7/018 5/600 |
| 2013/0142367 A1 | 6/2013 | Berry et al. | |
| 2014/0259414 A1* | 9/2014 | Hayes | ................. A61B 5/6892 5/611 |
| 2014/0320290 A1* | 10/2014 | Reeder | ................. A61B 5/0002 340/573.1 |
| 2015/0135436 A1 | 5/2015 | Stryker et al. | |
| 2015/0239365 A1 | 8/2015 | Hyde et al. | |
| 2015/0281659 A1* | 10/2015 | Hood | ..................... A61G 7/018 348/143 |
| 2016/0259906 A1* | 9/2016 | Iucha | ................. G06F 19/3412 |
| 2016/0283681 A1 | 9/2016 | Falck et al. | |
| 2016/0331614 A1 | 11/2016 | Furman et al. | |
| 2018/0161225 A1 | 6/2018 | Zerhusen et al. | |

FOREIGN PATENT DOCUMENTS

| | | |
|---|---|---|
| EP | 0553372 A1 | 1/1992 |
| WO | 9834577 | 8/1998 |
| WO | 2004021952 A2 | 3/2004 |

\* cited by examiner

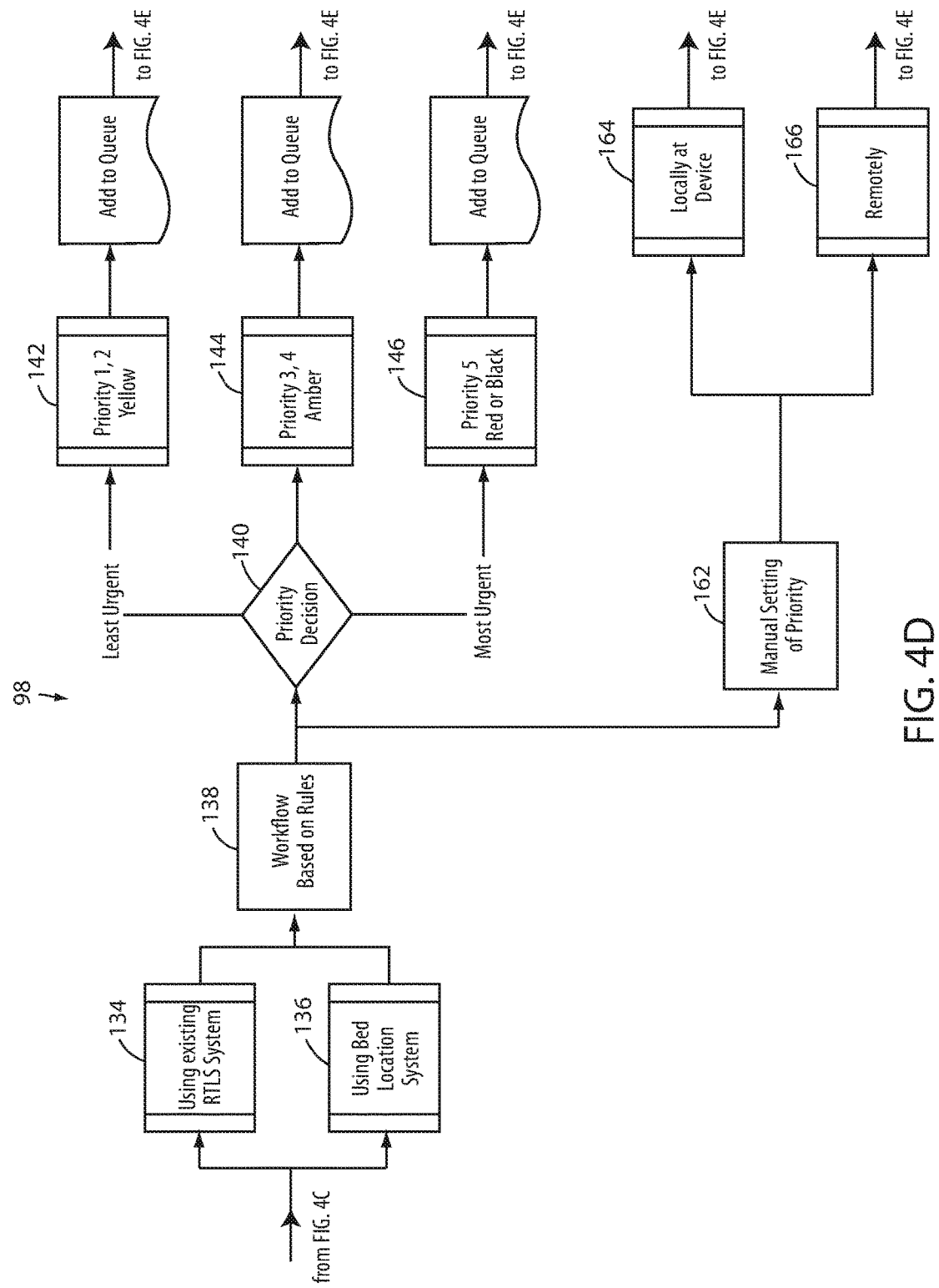

SERVICE SCHEDULING AND NOTIFICATION SYSTEMS FOR PATIENT SUPPORT APPARATUSES

This application claims priority to U.S. provisional patent application Ser. No. 62/410,869 file Oct. 21, 2016, by inventors Krishna Bhimavarapu et al. and entitled SERVICE SCHEDULING AND NOTIFICATION SYSTEMS FOR PATIENT SUPPORT APPARATUSES, the complete disclosure of which is hereby incorporated herein by reference.

BACKGROUND

The present disclosure relates to patient support apparatuses—such as beds, stretchers, cots, and the like—and more particularly to systems and methods for handling the servicing of such patient support apparatuses.

Patient support apparatuses are used in healthcare facilities, such as hospitals and the like, to support patients. As with all medical equipment, patient support apparatuses need to be occasionally serviced, either as part of a routine maintenance schedule, or in response to issues arising from one or more components. Performing such servicing can be challenging for technicians because the healthcare facility may continue to use the patient support apparatuses when they are in need of servicing, thereby preventing the technician from performing the required servicing because such servicing is typically only performed when the patient support apparatus is not being used.

SUMMARY

The present disclosure provides systems and methods for improving the servicing of patient support apparatuses and/or other equipment. According to various aspects, the systems and methods coordinate the availability of patient support apparatuses for servicing with the arrival of a technician; help the technician plan his or her servicing schedule while at the healthcare facility; help the healthcare facility continue to use patient support apparatuses needing low priority service until the technician arrives, thereby providing the healthcare facility with more efficient usage of their patient support apparatuses; and prevent the healthcare facility from using patient support apparatuses that are in need of high priority service. Still other features and advantages are discussed in greater detail below.

According to one embodiment, a patient support apparatus is provided that includes a frame, a support surface, and a controller. The support surface is supported on the frame and adapted to support a patient thereon. The controller provides notification to a user of a service event relating to the patient support apparatus, and the controller further limits functionality of a component of the patient support apparatus based upon a severity of the service event.

According to other aspects, the severity of the service event is determined by a remote device in communication with the controller or, in other embodiments, by the patient support apparatus itself.

In some embodiments, the severity of the service event is categorized according to at least three levels. A first one of the three levels corresponds to a high priority level, a second one of the three levels corresponds to a medium priority level, and a third one of the three levels corresponds to a low priority level.

When three or more levels are provided, the controller is configured in some embodiments to not limit functionality of the component of the patient support apparatus if the service event corresponds to a low priority level. The controller, however, may limit functionality of the component of the patient support apparatus if the service event corresponds to a medium priority level. Further, the controller may completely eliminate functionality of the component if the service event corresponds to a high priority level.

In some embodiments, the service event relates to service needed for a second component of the patient support apparatus that is different from the component whose functionality is limited.

The controller may be configured to detect the service event, or the service event may be detected by a remote device in communication with the controller.

The service event, in some embodiments, is a detection of a condition of the patient support apparatus warranting service by a service person. Alternatively, the service event, in other embodiments, is a scheduling of a time at which the patient support apparatus is to be serviced by a service person, or an arrival of a time window associated with a scheduled service time of the patient support apparatus. The time window is adjustable by a user, in some embodiments.

The component whose functionality is limited is a motor, in some embodiments, and the controller prevents the motor from operating in at least one direction.

In other embodiments, the service event relates to a load cell of the patient support apparatus and the controller limits functionality of a scale of the patient support apparatus by preventing a weight measurement from being taken.

In still other embodiments, the service event relates to a load cell of the patient support apparatus and the controller limits functionality of an exit detection system of the patient support apparatus by preventing the exit detection system from being armed.

A user interface is provided on the patient support apparatus in some embodiments. The user interface enables a user to change a state of the patient support apparatus from an in-use state to a ready-for-service state. In some such embodiments, the service event is the user changing the state of the patient support apparatus to the ready-for-service state. The controller may send a message to a remote device in response to the user changing the state of the patient support apparatus. The message indicates the current state of the patient support apparatus.

According to still other aspects, the patient support apparatus includes a visual indicator that is illuminated when a control on the patient support apparatus is activated. The control is for controlling a function of the patient support apparatus other than the illumination of the visual indicator, and the illumination of the visual indicator thereby provides a visual indication of limited functionality to the user.

According to another embodiment, a patient support apparatus is provided that includes a frame, a support surface, a first control, and a controller. The first control is for carrying out a first function of the patient support apparatus. The controller detects when the first control is activated by a user and, in response to such activation, determines whether the patient support apparatus has been marked for use or marked for servicing. If the patient support apparatus has been marked for use, the controller responds to the activation of the first control in a first manner. If the patient support apparatus has been marked for service, the controller responds to the activation of the first control in second manner that is different from the first manner.

According to other aspects, the first manner includes carrying out the first function of the patient support apparatus and the second manner includes not carrying out the first function of the patient support apparatus.

Alternatively, the first manner includes carrying out the first function of the patient support apparatus and the second manner includes carrying out the first function of the patient support apparatus simultaneously with a second function of the patient support apparatus.

As another alternative, the first manner includes carrying out the first function of the patient support apparatus without a predetermined limit, and the second manner includes carrying out the first function of the patient support apparatus with the predetermined limit.

As yet another alternative, the first manner includes carrying out the first function of the patient support apparatus and the second manner includes carrying out the first function of the patient support apparatus and changing how the controller reacts to a subsequent activation of a second control for carrying out a second function of the patient support apparatus.

The second function, in some embodiments, includes providing a visual indication to the user that the patient support apparatus has been marked for service. The visual indication may be provided by illuminating a light that is not illuminated when the first function is carried out in the first manner.

The second function, in some embodiments, includes displaying on a display of the patient support apparatus a time at which service has been scheduled for the patient support apparatus.

The patient support apparatus also includes, in some embodiments, a second control adapted to allow a user to mark the patient support apparatus for service. The controller may restrict use of the second control to authorized users. The second control is accessed via a user interface on board the patient support apparatus in some embodiments, and the controller restricts use of the second control by requiring a passcode.

According to other aspects, the patient support apparatus includes a transceiver for communicating with a remote device, and the patient support apparatus is able to be marked for service in response to a message received from the remote device.

Alternatively, or additionally, the controller marks the patient support apparatus for service based upon data received from a sensor on board the patient support.

The second manner in which the controller responds to the activation of the first control varies, in some embodiments, based upon a comparison of a current time and date with a scheduled service time and date. The second manner may include not carrying out the first function if the current time and date fall within a time window associated with the scheduled service time and date. The second manner may also vary based upon a severity level associated with the service for which the patient support apparatus has been marked.

The patient support apparatus also includes, in some embodiments, a second control that allows a user to mark the patient support apparatus as available for servicing.

The first control may be a button wherein the first function activates a motor onboard the patient support apparatus.

According to another embodiment, a computer-implemented method for managing a plurality of patient support apparatuses in a medical facility is provided. The method includes executing on one or more processors the following steps: receiving data indicating that a first patient support apparatus has been scheduled for service, and sending a message to the first patient support apparatus indicating it has been scheduled for service. The message causes the first patient support apparatus to provide an indication to a user that the first patient support apparatus has been scheduled for service.

According to other aspects, the method further includes receiving usage data from the plurality of patient support apparatuses; analyzing the usage data; and determining if a second patient support apparatus of the plurality of patient support apparatuses should be serviced.

In some embodiments, the data indicating that the first patient support apparatus has been scheduled for service is received from a computer application in communication with a local area network. The computer application may be executed on a mobile computing device able to be carried by a user. The mobile computing device is, in some embodiments, a smart phone, tablet computer, or a laptop computer.

In other embodiments, the method further includes receiving additional data indicating that a second patient support apparatus has been scheduled for service, and sending a message to the second patient support apparatus indicating it has been scheduled for service. The message causes the second patient support apparatus to provide an indication to a user that the second patient support apparatus has been scheduled for service. In such embodiments, the method may further include generating a suggested order in which the first and second patient support apparatuses should be serviced. Still further, in such embodiments, the method may also include receiving location data indicating a location of the first and second patient support apparatuses, receiving availability for servicing data from each of the first and second patient support apparatuses, and using the location data and availability for servicing data to generate the suggested order in which the first and second patient support apparatuses should be serviced.

In some embodiments, the method also includes sending a second message to the first patient support apparatus instructing the first patient support apparatus to change to an unusable configuration until servicing of the first patient support apparatus commences.

According to another embodiment, a computer-implemented method for managing a plurality of patient support apparatuses in a medical facility is provided. The method includes receiving first data indicating that a first patient support apparatus has been scheduled for service; receiving second data indicating that a second patient support apparatus has been scheduled for service; and generating a suggested order in which the first and second patient support apparatuses should be serviced.

According to other aspects, the method further includes receiving location data indicating a location of the first and second patient support apparatuses; receiving servicing availability data from each of the first and second patient support apparatuses; and using the location data and servicing availability data to generate the suggested order in which the first and second patient support apparatuses should be serviced.

The method also includes, in some embodiments, receiving technician data indicating a technician's presence at the medical facility; determining which ones of the other patient support apparatuses are available for service; and generating a list of the other patient support apparatuses that are available for service.

In still other embodiments, the method also includes communicating a time at which the first patient support apparatus has been scheduled for service to the first patient support apparatus; and communicating a time at which the second patient support apparatus has been scheduled for service to the second patient support apparatus. In some such embodiments, the first patient support apparatus displays the time at which it has been scheduled for service on its display; and the second patient support apparatus displays the time at which it has been scheduled for service on its display.

The method may also or alternatively include sending a message to the first patient support apparatus instructing the first patient support apparatus to change to an unusable configuration until servicing of the first patient support apparatus commences. The unusable configuration may include locking a plurality of motors on the patient support apparatus.

According to still another embodiment, a computer-implemented method for managing a plurality of patient support apparatuses in a medical facility is provided. The method includes receiving usage data from the plurality of patient support apparatuses; analyzing the usage data; determining if any of the patient support apparatuses should be marked for service based on the analyzed usage data; and if at least one of the patient support apparatuses should be marked for service, sending a message to a computer located remote from the medical facility.

In other aspects, the method includes sending service type data to the remote computer. The service type data indicates a type of service which should be performed on a corresponding patient support apparatus (e.g. replace, repair, lubricate, calibrate, etc.). The service type data may also include data indicating an identity of a component needing replacement on the corresponding patient support apparatus.

In some embodiments, the computer is located remote from the medical facility is a computer located at a service center.

The method may also include interrogating an inventory control computer to determine if a replacement component is on-site at the medical facility. The replacement component is a replacement for the component needing replacement on the corresponding patient support apparatus.

According to still another embodiment of the present disclosure, a computer-implemented method for managing a plurality of patient support apparatuses in a medical facility is provided. The method includes receiving data indicating a first patient support apparatus is in need of service; determining a priority level associated with the service in which the first patient support apparatus is in need; and if the priority level exceeds a predetermined level, sending a message to the first patient support apparatus instructing the first patient support apparatus to change to an unusable configuration until servicing of the first patient support apparatus commences.

In other aspects, the method includes interrogating a tracking server prior to sending the message. The tracking server provides information indicating whether the first patient support apparatus is currently assigned to a patient or not. The method may also include delaying the sending of the message to the first patient support apparatus until the tracking server indicates the first patient support apparatus is not currently assigned to a patient.

In some embodiments, the method includes determining if a current time and date fall within a time window associated with a scheduled service time and date for the first patient support apparatus, and sending the message to the first patient support apparatus if the current time and date fall within the time window.

The data indicating the first patient support apparatus is in need of service may be received from a database that includes records indicating a previous time and date of service and a recommended service interval between service dates.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 4D is a fourth portion of the flow diagram of FIG. 4A;

DETAILED DESCRIPTION OF THE EMBODIMENTS

Figure 1:
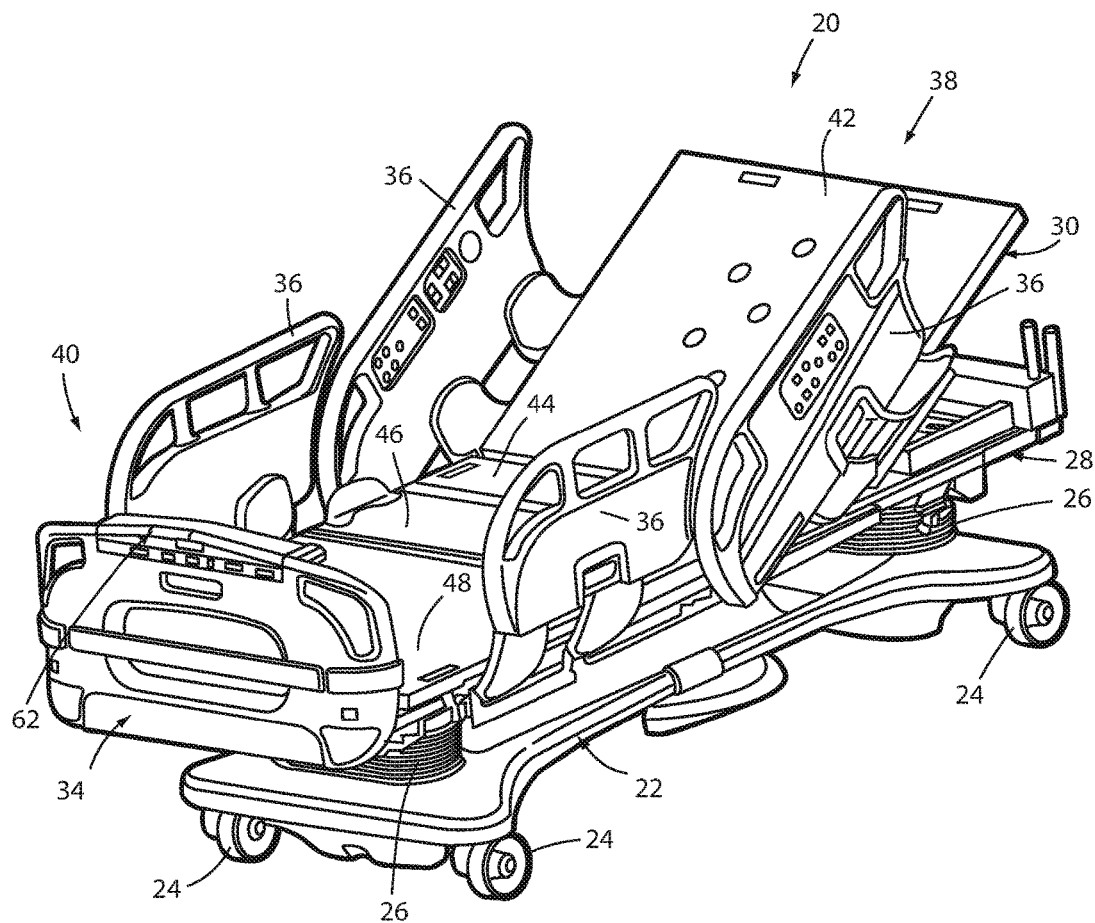
FIG. 1 is a perspective view of an illustrative patient support apparatus incorporating one or more of the various features of the present disclosure.

An illustrative patient support apparatus 20 that incorporates one or more aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, an operating table, or any other structure capable of supporting a person, whether stationary or mobile.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a headboard (not shown), a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

The mechanical construction of patient support apparatus 20 may be the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on forms different from what is disclosed in the aforementioned references.

Figure 2:
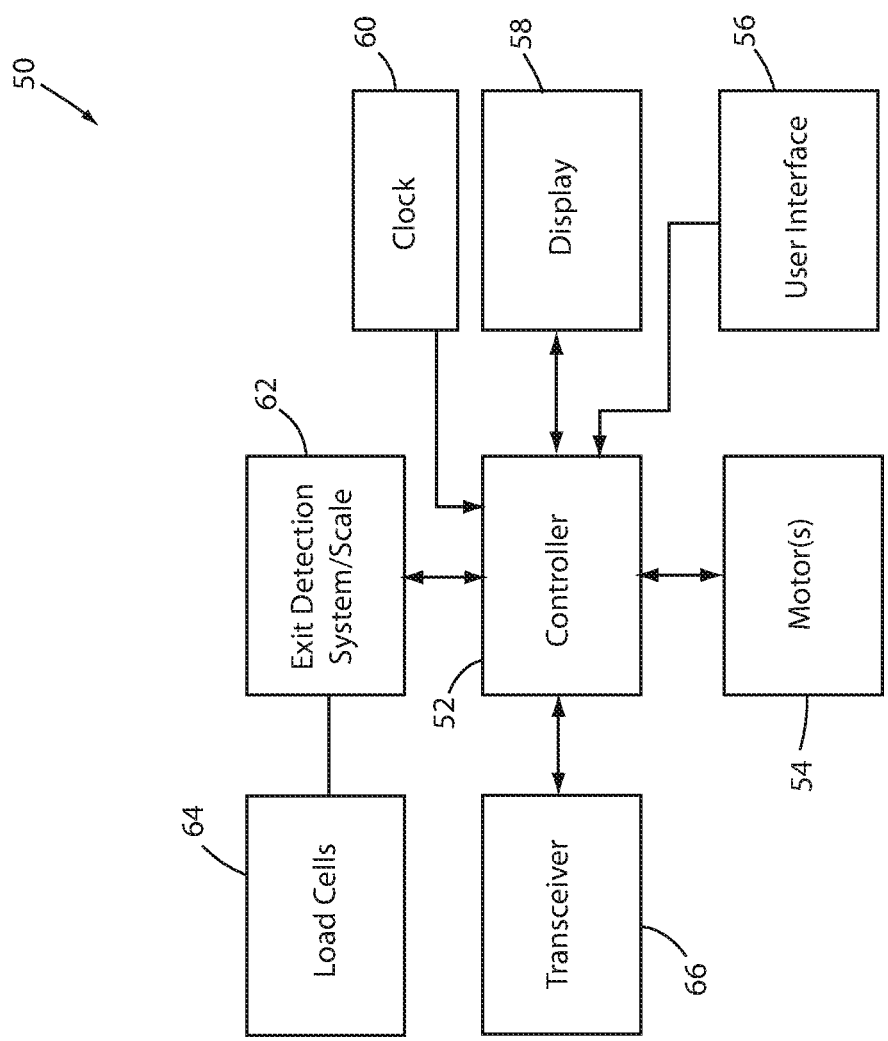
FIG. 2 is a diagram of a control system according to one embodiment that may be implemented in various patient support apparatuses, such as, but not limited to, the one of FIG. 1.

As shown more clearly in FIG. 2, patient support apparatus 20 includes a control system 50 having a controller 52, one or more motors 54, a user interface 56, a display 58, a clock 60, an exit detection system and/or scale 62 having a plurality of load cells 64, and a transceiver 66. Control system 50 controls a plurality of different aspects of patient support apparatus 20 and, as will be discussed in more detail below, takes one or more actions in response to a service event that is detected with respect to patient support apparatus 20.

Controller 52 (FIG. 2) is constructed of any electrical component, or group of electrical components, that are capable of carrying out the functions described herein. In many embodiments, controller 52 is a conventional microcontroller, although not all such embodiments need include a microcontroller. In general, controller 52 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 52 in carrying out the functions described herein, as well as the data necessary for carrying out these functions, are stored in a memory (not labeled) accessible to controller 52.

Motors 54 (FIG. 2) are used to move one or more components of patient support apparatus 20 and operate under the control of controller 52. In some embodiments, one or more motors 54 are incorporated into one or more linear actuators. Motors 54 may be used to power lifts 26, pivot head section 42, pivot foot section 48 and/or thigh section 46, drive one or more powered wheels on patient support apparatus 20 for facilitating transport of patient support apparatus 20 to different locations, and/or for still other purposes.

User interface 56 (FIG. 2) communicates with controller 52 and enables a user of patient support apparatus 20 to control one or more aspects of patient support apparatus 20, including exit detection system/scale 62 (discussed below). User interface 56 is implemented in the embodiment shown in FIG. 1 as a control panel having a lid (flipped down in FIG. 1) underneath which is positioned a plurality of controls. The controls—which may be buttons, dials, switches, or other devices—allows a user to control various aspects of patient support apparatus 20, such as, but not limited to, moving one or more components of patient support apparatus 20 (via motors 54), selecting one or more functions carried out by controller 52 (e.g. monitoring patient activity, turns, movement, etc.), taking a weight reading of the patient via exit detection/scale system 62, selecting a mode of operation of exit detection/scale system 62 and/or arming and disarming exit detection/scale system 62. Although FIG. 1 illustrates user interface 56 mounted to footboard 34, it will be understood that user interface 56 can be positioned elsewhere, and/or that one or more additional user interfaces can be added to patient support apparatus 20 in different locations, such as the siderails 36, for controlling various aspects of patient support apparatus 20.

Display 58 (FIG. 2) is also in communication with controller 52 and is adapted to display information regarding patient support apparatus 20. Display 58 is a Liquid Crystal Display (LCD), in some embodiments. In other embodiments, display 58 may be a cathodoluminescent display (e.g. a Cathode Ray Tube (CRT) display), an electroluminescent display (e.g. an Active-Matrix organic light-emitting diode (AMOLED) display), a photoluminescent display (e.g. a plasma display), and/or an incandescent display (e.g. a seven segment display). In still other embodiments, display 58 includes touch screen technology associated with it and reacts to touches on the surface of display 58. It will also be understood that, in some embodiments of patient support apparatus 20, more than one display 58 may be included.

Clock 60 (FIG. 2) is a clock used by controller 52 to keep track of both the time of day and the date. As will be discussed in greater detail below, controller 52 uses clock 60 for keeping track of and/or scheduling tasks associated with the servicing of patient support apparatus 20. In some embodiments, clock 60 is updated and operates in one of the manners disclosed in commonly assigned U.S. patent application Ser. No. 62/361,092 filed Jul. 12, 2016, by inventors Anuj Sidhu et al. and entitled PATIENT SUPPORT APPARATUSES WITH CLOCKS, the complete disclosure of which is hereby incorporated herein by reference. Other types of clocks can of course be used.

Exit detection/scale system 62 includes a plurality of force sensors that detect downward forces exerted by the patient onto patient support apparatus 20. In the illustrated embodiment (FIG. 2), the force sensors are implemented as load cells 64. However, it will be understood that other types of force sensors may be used. Indeed, in some embodiments, the exit detection function of system 62 is carried out using no force sensors, such as by using one or more video cameras, as disclosed in commonly assigned U.S. patent application Ser. No. 14/578,630, filed Dec. 22, 2014, by inventors Richard Derenne et al. and entitled VIDEO MONITORING SYSTEM, or by using one or more accelerometers, such as disclosed in commonly assigned U.S. patent application Ser. No. 62/253,167 filed Nov. 11, 2015, by inventors Marko Kostic et al. and entitled PATIENT SUPPORT APPARATUSES WITH ACCELERATION DETECTION, the complete disclosures of both of which are hereby incorporated herein by reference.

Load cells 64 detect downward forces exerted by an occupant of support deck 30. Thus, when an occupant is positioned on support deck 30 and substantially still (i.e. not moving in a manner involving accelerations that cause forces to be exerted against support deck 30), load cells 64 detect the weight of the occupant (as well as the weight of any components of patient support apparatus 20 that are supported—directly or indirectly—by force sensors 64). Exit detection/scale system 62 is thereby able to perform the scale function of measuring the weight of the patient, or other occupant, of patient support apparatus 20.

The exit detection function of system 62 determines when an occupant of patient support apparatus 20 is likely to exit patient support apparatus 20. More specifically, system 62 is adapted to determine when an occupant is likely to leave prior to the occupant actually leaving, and to issue an alert and/or notification to appropriate personnel so that proper steps can be taken in response to the occupant's imminent departure in a timely fashion. In some embodiments, exit detection is performed by determining a center of gravity of the occupant (based upon the outputs and known relative locations of load cells 64) in order to determine if the occupant is about to exit patient support apparatus 20. In one such embodiment, exit detection/scale system 62 determines this center of gravity using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference.

In other embodiments, other algorithms may be used to determine if the patient is about to exit from patient support apparatus 20. For example, in one such alternative embodiment, the outputs from load cells 64 are analyzed, not to determine a center of gravity, but instead to determine one or more ratios of the relative weights sensed by the load cells 64 (e.g. the weight of the left side load cells 64 compared to the total weight, or the weight of the right side load cells compared to the total weight, or still other ratios) and those ratios are used to determine if the occupant is about to exit patient support apparatus 20.

Figure 3:
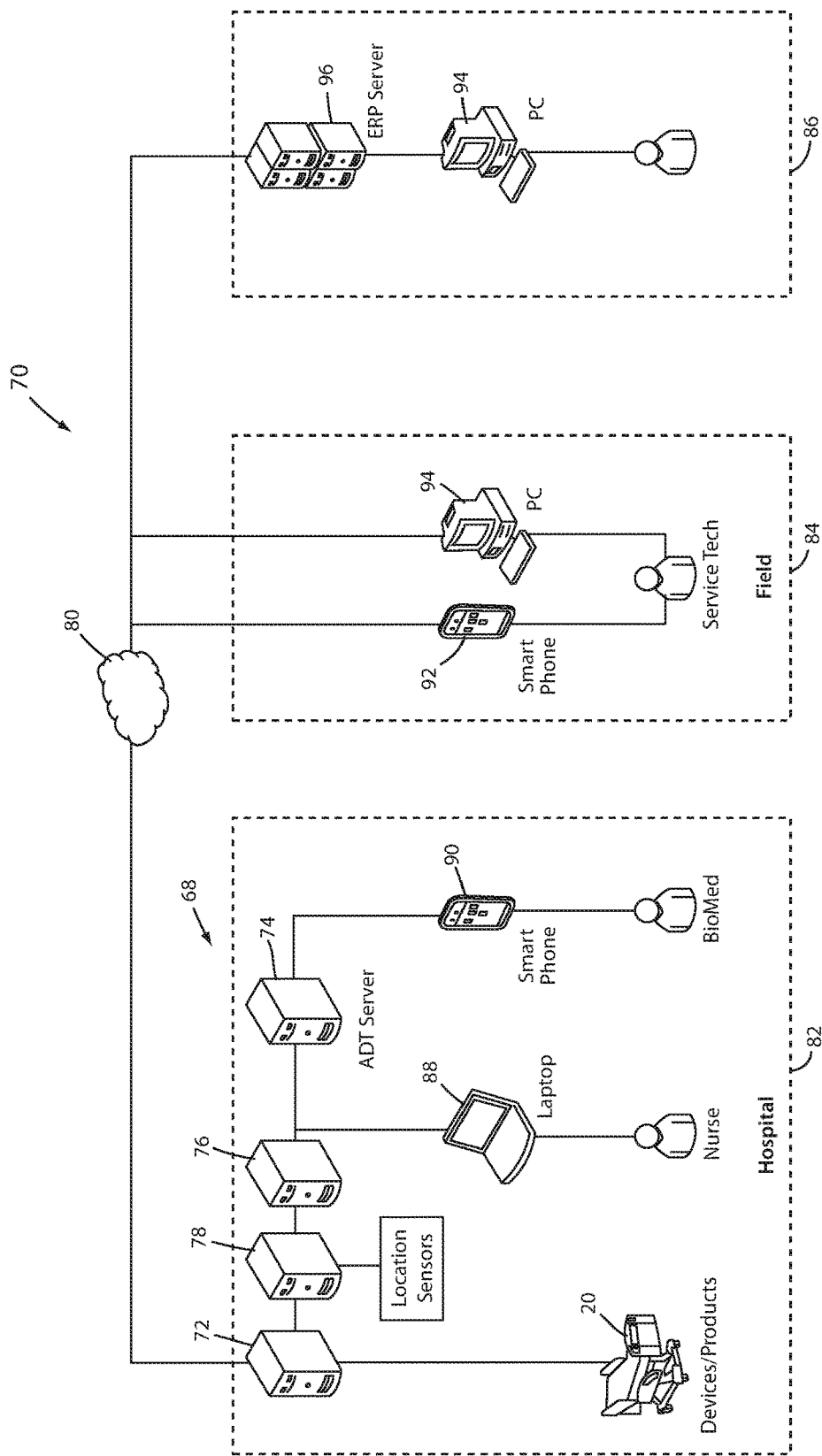
FIG. 3 is diagram of a patient support apparatus servicing system according to one embodiment.

Transceiver 66 (FIG. 2) is used to communicate with one or more off-board devices. Transceiver 66 may be coupled to a port for receiving one or more wires or cables, or it may be a wireless transceiver coupled to an antenna, or other wireless transmitting means (e.g. infrared transmitter). In some embodiments, one or more transceivers 66 are included that communicate both via wire and wirelessly. When a port is included, the port may be an Ethernet port for coupling to an Ethernet cable that is coupled to a healthcare facility computer network 68 (FIG. 3). In alternative embodiments, the port may be a serial port, such as for a Universal Serial Bus (USB), that communicates with one or more computers of the healthcare facility computer network 68. If transceiver 66 is a wireless transceiver, it may be a WiFi transceiver (IEEE 802.11) that communicates with one or more wireless access points of the healthcare facility network 68. Alternatively, transceiver 66 may be implemented as a wireless ZigBee transceiver (IEEE 802.15.4) or a wireless Bluetooth transceiver (IEEE 802.15.1). Still other types of transceivers may be used. In still other embodiments, transceiver 66 may be adapted to communicate with a headwall structure that forwards messages received from patient support apparatus 20 to server 72. One such suitable headwall structure is disclosed in commonly assigned U.S. patent application Ser. No. 14/819,844 issued Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

FIG. 3 illustrates in greater detail one embodiment of a servicing system 70 according to one embodiment of the present disclosure. Servicing system 70 is implemented in a healthcare facility 82 and in communication with both a service center 84 and a manufacturing entity 86 in the embodiment shown in FIG. 3. Servicing system 70 may be implemented in other manners from what is shown in FIG. 3. For example, in some embodiments, servicing system 70 includes more than one service center 84. In other embodiments, servicing system 70 does not communicate with manufacturing entity 86. In still other embodiments, servicing system 70 is located entirely within healthcare facility 82 and does not utilize any external computing resources. Still other variations are possible.

The portion of servicing system 70 located within healthcare facility 82 includes one or more patient support apparatuses 20, a patient support apparatus server 72, a conventional Admission, Discharge, and Transfer (ADT) server 74, and an inventory control server 76. In some embodiments, computer network 68 may also include a location and/or tracking server 78. Although FIG. 3 illustrates servers 72, 74, 76, and 78 as hardware servers, this is merely illustrative of one manner of embodying servers 72, 74, 76, and/or 78. In other embodiments, one or more of servers 72, 74, 76, and 78 are software servers. Further, when implemented as software servers, one or more of the software servers may operate on a common piece of server hardware, or they may operate on separate hardware servers.

Regardless of whether they are implemented as hardware or software servers, servers 72, 74, 76, and 78 are part of healthcare facility computer network 68. Patient support apparatuses 20 communicate with patient support apparatus server 72 via transceiver 66. Communications received from patient support apparatuses 20 by patient support apparatus server 72 are forwarded, as appropriate, to one or more other servers on computer network 68, or to other devices, as will be described in more detail below.

Healthcare facility computer network 68 is in communication with the Internet 80 (FIG. 3). This communication enables patient support apparatus server 72 (as well as the other servers of computer network 68) to communicate with field service center 84 and manufacturing entity 86. Field service center 84 comprises one or more geographic locations where service personnel associated with patient support apparatuses 20 are located, and/or where components used to service patient support apparatus 20 are located. Manufacturing entity 86 corresponds to a location associated with the manufacturer of patient support apparatuses 20 and may particularly be the sales/service department of the manufacturer of patient support apparatuses 20.

Inside of healthcare facility 82, one or more computers 88 and/or one or more smart phone 90 are in communication with computer network 68. Such communications may take place in any conventional manner, such as, but not limited to, WiFi connections between the network 68 and each of the computers 88 and smart phones 90. The connections between network 68 and each of computers 88 and smart phones 90 enables the users of computers 88 and smart phones 90 to communicate with patient support apparatus server 72. As noted, patient support apparatus server 72 communicates with patient support apparatuses 20 and receives and transmits data regarding the servicing of patient support apparatuses 20. As will be discussed in greater detail below, in addition to gathering service data from the patient support apparatuses 20, patient support apparatus server 72 also communicates with other servers on computer network 68 (e.g. 74, 76, and/or 78) as well as one or more computers 88 and/or smart phones 90, thereby allowing users of computers 88 and smart phones 90 to receive service data from server 72 and to send service data and/or commands to server 72.

Patient support apparatus server 72 is further configured to communicate with one or more remote smart phones 92 and/or remote computers 94 that are located outside of healthcare facility 82. Such remote computers 94 and smart phones 92 may be located at service center 84, manufacturing entity 86, and/or at any other locations having Internet access that enables these devices to communicate with patient support apparatus server 72. As shown in FIG. 3, in some instances, the computer 94 that communicates remotely with patient support apparatus server 72 may be coupled to one or more intermediary servers 96. Such intermediary servers 96 act as conduits for passing messages back and forth between server 72 and the computer(s) 94. In one embodiment, intermediary server 96 is an Enterprise Resource Planning (ERP) server.

In general, servicing system 70 operates to perform one or more of the following functions: monitor the use of patient support apparatuses 20 and determine when one or more service events associated with one or more patient support apparatuses 20 occur; provide notifications to appropriate personnel when such a service event occurs; assess a priority level of the service events; reduce the functionality of one or more patient support apparatuses 20 in response to a service event that has a high priority level (or in response to other data regarding the service event); cause the patient support apparatuses 20 to display a message, or other information, on display(s) 58 regarding the servicing event; schedule times for servicing of the patient support apparatuses 20 to occur; schedule an order in which multiple patient support apparatuses 20 are to be serviced during a service visit; check the availability of one or more replacement parts at one or more locations; order one or more replacement parts, if needed; and/or share servicing information with users positioned remotely from hospital and/or outside of the rooms in which the patient support apparatuses 20 are currently located (via computers 88, 94 and/or smart phones 90, 92). Still other functions may be carried out as described in more detail below.

FIGS. 4A-4I illustrate in greater detail one example of a flow diagram for servicing method 98 that may be carried out by servicing system 70. It will be understood that although the flow diagram of FIGS. 4A-4I illustrates only one illustrative embodiment of servicing method 98, flow method 98 may be varied from the specific steps set forth in these figures. Thus, the embodiment shown in these figures can be modified to include any subset of the steps shown therein, and/or to include one or more additional and/or alternative steps.

Figure 4A:
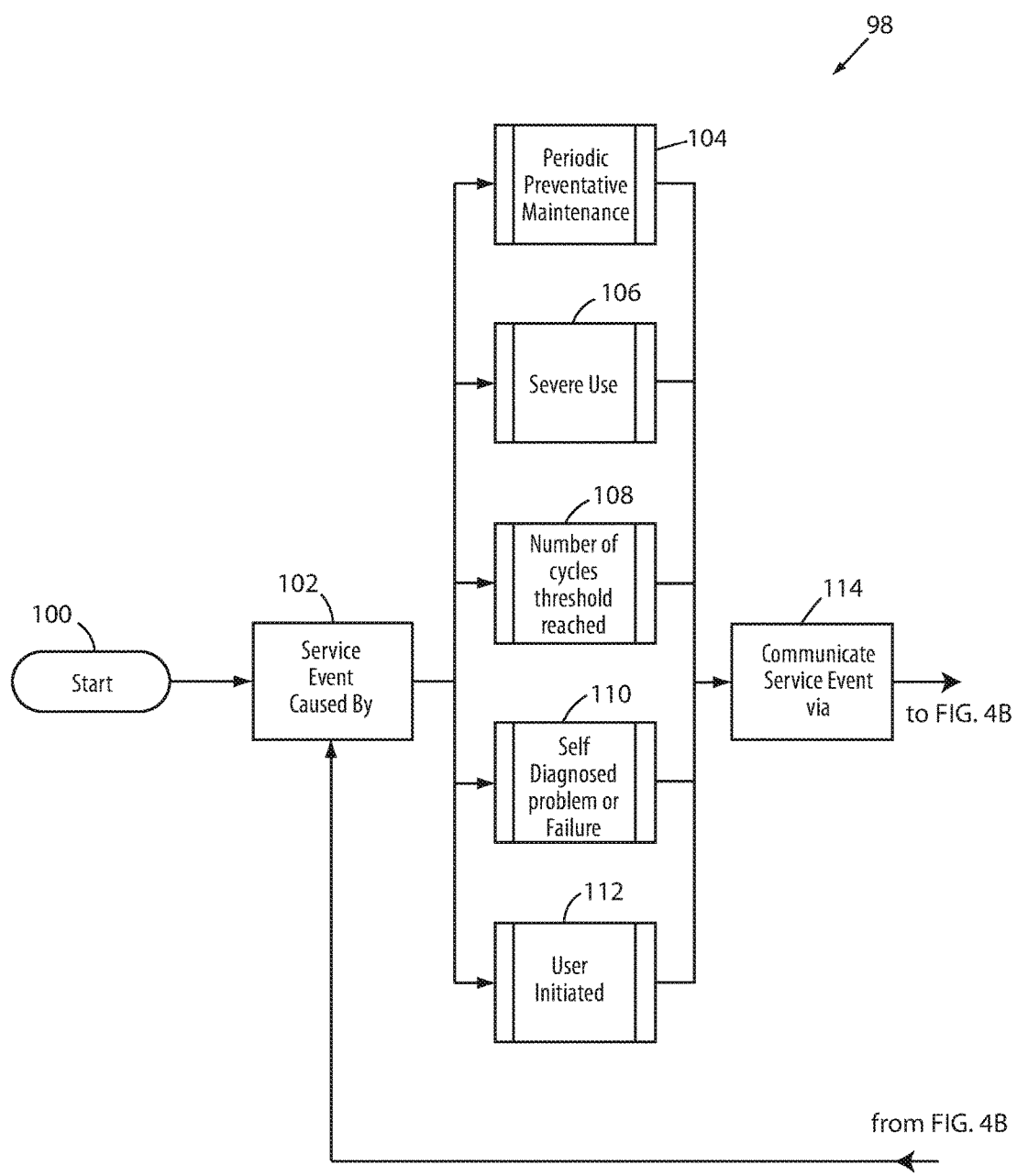
FIG. 4A is a first portion of a flow diagram for a servicing method according to one embodiment of the present disclosure.

Servicing method 98 begins at a start step 100 (FIG. 4A). Commencement of servicing method 98 may begin automatically in response to a patient support apparatus 20 being turned on (i.e. plugged into a source of electrical energy or operating under battery power), a switch or other control being activated on patient support apparatus 20, and/or it may begin automatically in response to patient support apparatus server 72 executing appropriately programmed software for carrying out the functions described herein. In other embodiments, either or both of these devices (patient support apparatus 20 and patient support apparatus server 72) may be configured to allow a user to start or stop servicing method 98 as desired by an authorized user. Indeed, in some embodiments, system 70 can be configured to operate in conjunction with all, or any user-selected subset, of the patient support apparatuses 20 at a particular healthcare facility, or group of healthcare facilities 82.

After commencing at step 100, method 98 proceeds to a service event detection step 102 (FIG. 4A). Service event detection step 102 is carried out by each controller 52 on board each patient support apparatus 20, in some embodiments. In other embodiments, service event detection step 102 is carried out by server 72 based upon data transmitted thereto from the one or more patient support apparatuses 20. In still other embodiments, service event detection step 102 is carried out partially by controllers 52 and partially by server 72.

Controller 52 and/or server 72 carry out service event detection step 102 by monitoring one or more conditions or triggers to determine whether a service event has transpired. In the illustrated embodiment, there are five potential triggers that are monitored by controller 52 and/or server 72. These triggers include periodic preventative maintenance 104, severe usage 106, the meeting or exceeding of a cyclical usage threshold 108, self-diagnosis of a problem 110, and user initiation 112.

Controller 52 and/or server 72 monitor the periodic maintenance trigger 104 by monitoring the passage of time (e.g. via clock 60) and comparing the amount of time passed to a service schedule that is stored in memory accessible to controller 52 and/or server 72. The memory in which the service schedule is stored is positioned on-board patient support apparatus 20 in some embodiments. In other embodiments, the memory is included within server 72, while in still other embodiments, the service schedule is stored in multiple locations, or portions of it are stored on server 72 while other portions of it are stored on patient support apparatus(es) 20. In some embodiments, the service schedule is saved and stored on the memory of patient support apparatus 20 during the manufacture of patient support apparatus 20. In such embodiments, the service schedule may be different for each different type of patient support apparatus 20. In other embodiments, the service schedule is downloaded onto server 72 from one of the computers maintained at a service center 84 and/or the manufacturing entity 86. In still other embodiments, the service schedule is a dynamic service schedule that changes based upon data collected by one or more service centers 84 and/or by the manufacturer of the patient support apparatuses 20. When such dynamic service schedules are used, any updated service schedules may be communicated to server 72 using its Internet connection (or done locally at the healthcare facility 82) and the connection of service center 84 and/or manufacturing entity 86 to the Internet 80. Such dynamic service schedules are discussed more below with respect to FIG. 4C.

Wherever stored, and regardless of whether it is static or dynamic, the service schedule includes the recommended amount of time between servicing each of the components and/or systems of patient support apparatus that should receiving periodic maintenance. Such servicing may include lubricating one or more moving components of patient support apparatus 20, calibrating and/or re-testing of one or more sensors or other components (e.g. the load cells of exit detection 62), replacing one or more wear components, and/or other items. In addition to the service schedule, controller 52 and/or server 72 stores data indicating the last time each task listed on the service schedule was performed. Controller 52 and/or server 72 first determines the amount of time that has passed since the last performance of each task on the service schedule and compares that amount of time to the recommended amount of time in the service schedule for each of these tasks. If the recommended interval between servicing has been exceeded for one or more components, controller 52 and/or server 72 determines at step 100 that a servicing event has occurred and proceeds to step 114.

Controller 52 and/or server 72 monitor the presence or absence of a severe usage trigger 106 by keeping track of the loads that are applied to one or more components of the patient support apparatus 20 and comparing them to one or more thresholds. Such thresholds may be stored and updated in the same manner as the service schedule discussed above. Indeed, in some embodiments, these threshold are stored as part of the service schedule. The loads that controller 52 and/or server 72 monitor include a number of different loads, such as, but not limited to, the total weight supported on patient support apparatus 20 (as detected by load cells 64), the amount of current drawn by each of the various motors of patient support apparatus, and/or other items that are indicative of how hard one or more components are, and/or have been, driven. If controller 52 and/or server 72 detects that any component has been driven harder than the corresponding threshold, controller 52 and/or server 72 determine at step 102 that a servicing event has occurred and they proceed to step 114.

Controller 52 and/or server 72 monitor the presence or absence of a cycle threshold trigger 108 by keeping track of the cycles that each moving component and/or electrically powered function of patient support apparatus 20 experiences. For example, controller 52 and/or server 72 keeps track of how many times the lifts 26 of patient support apparatus 20 are activated; how many times the motors are activated that control the pivoting of the various sections of deck 30 (e.g. head section 42, seat section 44, thigh section 46, and/or foot section 48); how many times the exit detection function of system 62 is activated and/or detects an exit; how many times a weight reading is taken using the scale function of system 62; and/or how many times one or more other components or functions are used or activated. Controller 52 and/or server 72 compares the number of cycles for each of these actions with corresponding thresholds contained within the service schedule. These cyclical thresholds are different from the thresholds used for server usage trigger 106 discussed above. If the cyclical usage of one or more of these components or functions exceeds the corresponding cyclical threshold, controller 52 and/or server 72 determines that a service event has occurred and proceeds to step 114.

Controller 52 and/or server 72 monitor the presence or absence of a self-diagnosed trigger 110 by monitoring software (located onboard patient support apparatus 20 and/or on server 72) that analyzes the outputs from one or more components of patient support apparatus 20. Such software may be conventional self-diagnostic software, or it may be custom designed software that uses the outputs from one or more sensors on board patient support apparatus 20 to determine the absence or presence of a problem or failure with one or more components of patient support apparatus 20. Such sensors include, but are not limited to, electrical current sensors, voltage sensors, motion encoders, temperature sensors, and the like. If the self-diagnostic software detects a problem or failure with one or more components, controller 52 and/or server 72 determine that a service event has occurred and proceed to step 114. An indicator, such as a light, a sound, or a display of an image on a screen, may be triggered by controller 52 when such a problem or failure is detected. In some embodiments, the self diagnosis of an error or service event is detected in any of the manners disclosed in commonly assigned U.S. patent application Ser. No. 15/272,590 filed Sep. 22, 2016, by inventors Daniel Brosnan et al. and entitled UNIVERSAL CALIBRATION SYSTEM, the complete disclosure of which is incorporated herein by reference.

Controller 52 and/or server 72 monitors the presence or absence of a user-initiated service trigger 112 by monitoring user interface 56 on board patient support apparatus 20 and/or any other user interfaces that are able to communicate with controller 52 and/or server 72 (e.g. computers 88, 94 and/or smart phones 90, 92; FIG. 3). At least one of such user interfaces includes a control that allows an authorized user to request that one or more components or systems of the patient support apparatus 20 be serviced. In some embodiments, the user interface also allows the user to indicate a priority level of the desired servicing. Controller 52 and/or 72, in response to receiving such a user initiated request, proceeds to step 114.

At step 114 (FIG. 4A), controller 52 and/or server 72 communicates the existence of the detected service event (at step 102), as well as information regarding the type of service event and the cause of the service event, to a network server. If controller 52 is reporting the service event, the network server it reports the service event to is server 72. It does this by sending a message to server 72 indicating that a service event has occurred. If server 72 is reporting the event, the network server it reports the event to is one or more of the computers or servers located at service center 84 and/or manufacturing entity 86 (e.g. computers 88 or 94, or server 96). Server 72 reports this by sending a message to the one or more computers at service center 84 and/or manufacturing entity 86.

Figure 4B:
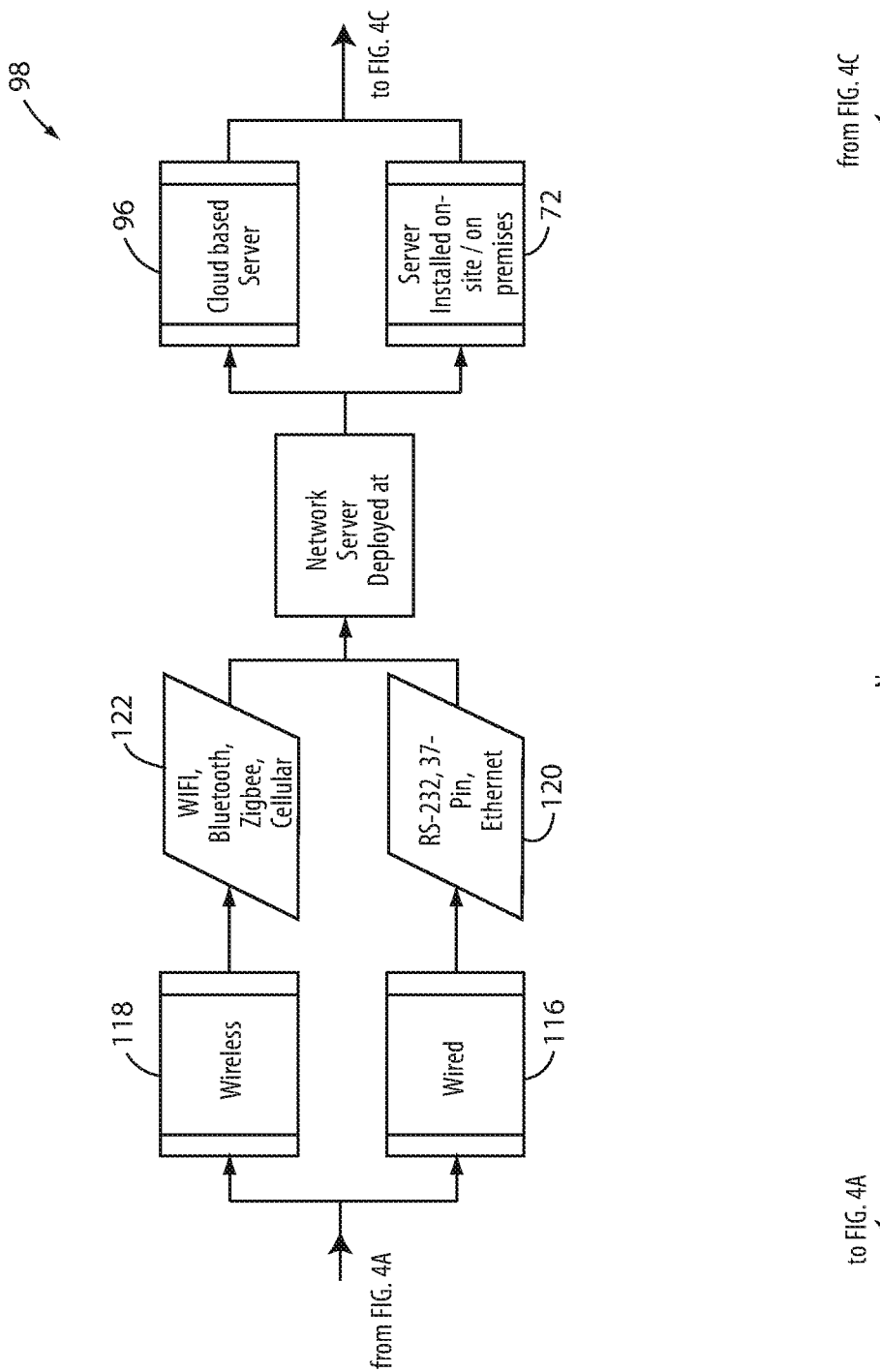
FIG. 4B is a second portion of the flow diagram of FIG. 4A.

As shown more clearly in FIG. 4B, the reporting of the service event may occur via a wired connection 116 or a wireless connection 118. As noted previously, wired connection 116 may be implemented as an RS-232 cable, a conventional 37-pin cable of the type commonly used in hospitals, as an Ethernet cable, a USB cable, or still other types of cables, as shown in box 120. Also as noted previously, wireless connection 118 may be implemented as a WiFi connection, a ZigBee connection, a Bluetooth connection, and/or a cellular connection, as shown by box 122.

As is also shown in FIG. 4B and was previously discussed, the reporting of the service event may be directed to a remote server (e.g. a cloud based server) such as intermediary server 96 or a server associated with service center 84, or it may be directed to an on-premises server, such as patient support apparatus server 72.

Figure 4C:
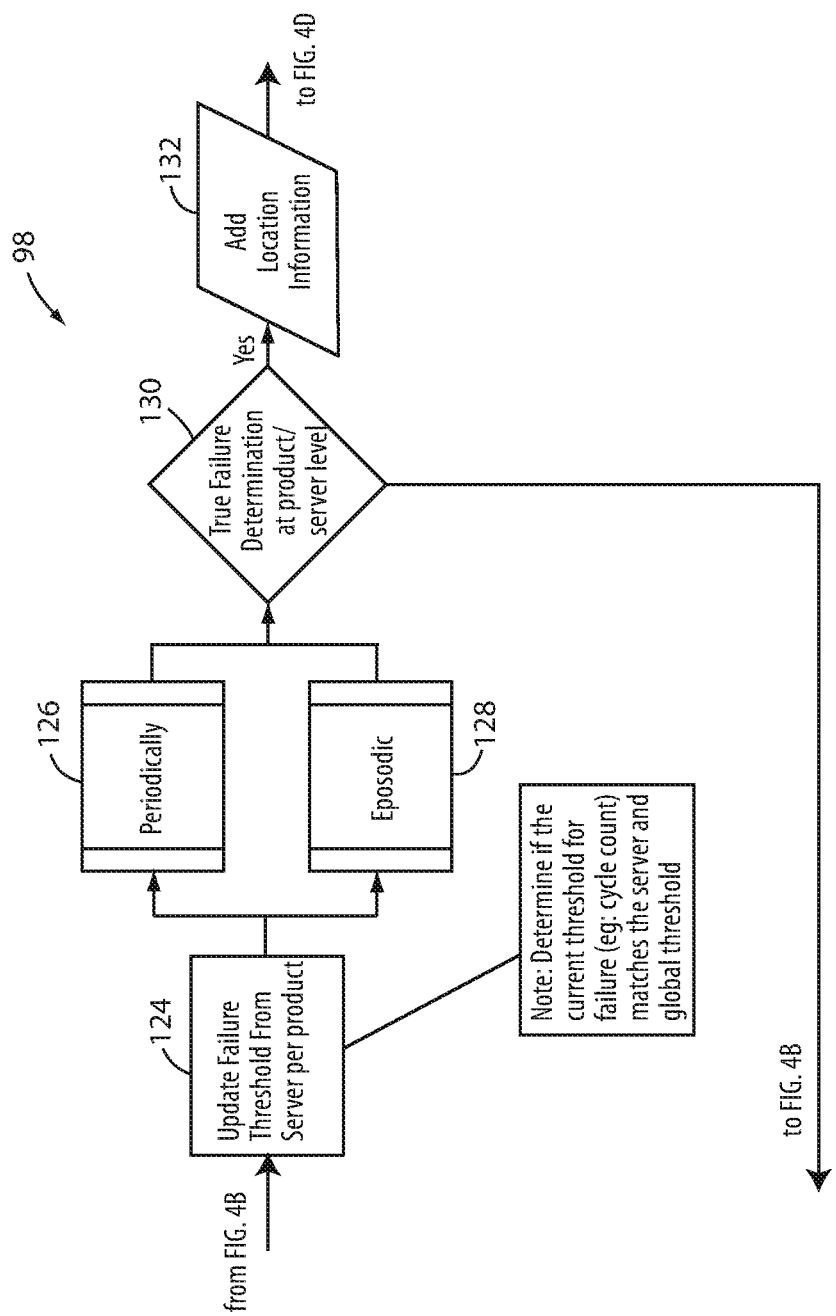
FIG. 4C is a third portion of the flow diagram of FIG. 4A.

From step 114, control proceeds to update step 124 (FIG. 4C). Update step 124 is carried out by the on-premise server 72 or by an off-premise server (such as, but not limited to, intermediary server 96). Update step 124 involves checking to ensure that the criteria for determining the service event are up to date. This is performed by comparing the service event data transmitted at step 114 to the latest service schedule data for that type of event. Thus, for example, if the service data transmitted at step 114 relates to a motor on board patient support apparatus 20 being activated more than X number of times (e.g. a cyclical trigger 108), update step 124 checks to see if the threshold X is the latest threshold for evaluating the service needs of that particular motor. Update step 124 is thus used when the service scheduling for a patient support apparatus 20 is based upon a dynamic service schedule. In some embodiments, servicing method 98 may operate without dynamic service schedules, in which case step 124 may be omitted.

Update step 124 is performed by communicating with intermediary server 96 to see if the manufacturer of patient support apparatus 20 has changed its recommended service schedule for the particular component(s) that were responsible for the service event detected at step 102. The manufacturing entity 86 initially sets the recommended service thresholds of the service schedule for the patient support apparatuses 20 and may, on occasion, make changes to those schedules based upon servicing trends, recalls, failures, or other information available to the manufacturing entity. In other embodiments, one or more service centers 84 may be authorized by the manufacturing entity 86 to make changes to the service schedule. In these situations, update step 124 is performed by receiving updated service scheduling data (via the Internet 80) from a computer or server associated with the authorized service center 84. Still further, in some embodiments, healthcare facility 82 is allowed to make changes to the service schedule. In such embodiments, update step 124 is performed by communicating with a designated healthcare server, such as server 76.

As shown in FIG. 4C, the updated service schedule information may be performed periodically, such as indicated by box 126, or it may be performed episodically, such as represented by box 128. When performed periodically, server 72 and/or an off-premises server make repetitive inquiries at predesignated intervals regarding whether the service schedule for the models of patient support apparatuses 20 that are located within healthcare facility 82 are up to date or not. When performed episodically, server 72 and/or the off-premises server makes inquiries regarding updated service schedule information in response to a service event being detected at step 102. That is, rather than performing repeated updates at regular intervals, the episodic updating occurs whenever a service event is detected.

After the completion of step 124, control proceeds to step 130 where on-premise server 72 and/or an off-premise server compares the service event data to the updated service schedule data to determine if a true servicing event has been detected. In other words, step 130 is similar to step 102 with the exception that step 130 ensures that the latest service schedule data is being used to determine the existence of a service event (while step 102 may, in some cases, utilize outdated service scheduling data).

In some embodiments, one or more authorized individuals associated with healthcare facility 82 may be allowed to customize the service scheduling data used by servicing system 70. That is, instead of, or in addition to, relying upon the service schedule developed by the manufacturer of patient support apparatuses 20 or one or more of its components, servicing system 70 can be modified to allow the healthcare facility 82 to create and/or adjust their own servicing schedule. In such instances, authorized representatives of the healthcare facility forward their own customized service schedule data to server 72 using one or more of the on-premise computers 88 and/or smart phones 90. Servicing method 98 then uses the customized service schedule data at steps 102 and/or 130. Further, in some embodiments, servicing method 98 may use a combination of both manufacturer-supplied service schedule data and healthcare facility-supplied service schedule data.

After the completion of step 130, control proceeds to step 132 where patient support apparatus server 72 (or an off-premise server, or the patient support apparatus 20 itself) determines the location of the patient support apparatus 20 experiencing the service event (FIG. 4C). This location determination is performed in one of two different manners. In a first manner, which is represented by box 134 (FIG. 4D), the location of patient support apparatus 20 is determined using a conventional Real-Time Locating Service (RTLS). In some embodiments, the RTLS uses asset tags that are attached to, among other things, patient support apparatuses 20. The asset tags may be RF ID tags, or other types of tags, which include unique identifiers. Transceivers positioned around the healthcare facility at known locations communicate with the asset tags and determine the locations of the assets (e.g. patient support apparatuses 20) to which the tags are attached. This location information is reported to location server 78. Location server 78 forwards this information to patient support apparatus server 72. Patient support apparatus server 72 is therefore informed of the position of each of the patient support apparatuses 20 in healthcare facility 82. Patient support apparatus server 72 receives a unique identifier from each patient support apparatus 20 for which a service event is detected and uses this unique identifier to correlate the location information received from location server 78. In some embodiments, the unique identifier is the same used by the RTLS system, while in other embodiments, server 72 includes a data table, or other data structure, that maps the identifiers received from the patient support apparatuses 20 via wired or wireless connections 116 or 118 with the identifiers received from location server 78.

In an alternative manner represented by box 136 (FIG. 4D), the location of each patient support apparatus 20 is determined by a location detection system that is specifically tailored to patient support apparatuses. Examples of such location detection systems are disclosed in commonly assigned U.S. Pat. No. 8,319,633 filed by Becker et al. and entitled LOCATION DETECTION SYSTEM FOR A PATIENT HANDLING DEVICE, the complete disclosure of which is hereby incorporated herein by reference. Other types of location detection systems may also be used, such as, but not limited to, those disclosed in commonly assigned U.S. patent application Ser. No. 14/578,630 filed Dec. 22, 2014, by inventors Richard Derenne et al. and entitled VIDEO MONITORING SYSTEM, the complete disclosure of which is also incorporated herein by reference. Still other types of location systems may also be used for identifying the location of each patient support apparatus 20 for which a service event has been detected.

After the location of the patient support apparatus 20 experiencing the service event has been determined using either the RTLS method of box 134 or the custom method of box 136, method 98 proceeds to step 138 where controller 52 and/or server 72 determines how to integrate the service event into the work flow at healthcare facility 82. More specifically, controller 52 and/or server 72 determines at step 138 whether the priority of the service event detected at step 102 should be determined automatically based upon preconfigured rules and programming, or manually based upon a user's instructions (FIG. 4D). If the priority level of the service event is to be determined automatically, method 98 proceeds to step 140. In the embodiment of method 98 shown in FIG. 4D, five different priority levels are used (1-5) that are treated in three different manners. This is merely illustrative and it will be understood that different numbers of priority levels and manners of treatment may be used. Any service events at priority levels 1 or 2 are assigned a low priority status as indicated by box 142. Any service events at priority levels 3 or 4 are assigned a medium priority status as indicated by box 144. Further, any service events at priority level 5 are assigned a high priority status as indicated by box 146.

The priority levels for the various service events may be determined in a variety of different manners. In some embodiments, the priority levels are determined ahead of time for each of the different service events that are possible and are stored in memory. In such cases the server 72 and/or other server accesses this memory, matches the current service event to the corresponding stored service event, and retrieves the priority level assigned to the current service event. In other embodiments, the priority levels are determined dynamically based upon one or more parameters that can be adjusted by the user, such as, but not limited to, the location of the service event, the usage level of the patient support apparatuses in the healthcare facility 82, the number of patient support apparatuses in the healthcare facility 82, the availability of replacement patient support apparatuses 20 or components thereof, the type of service event, and/or other factors.

Figure 4E:
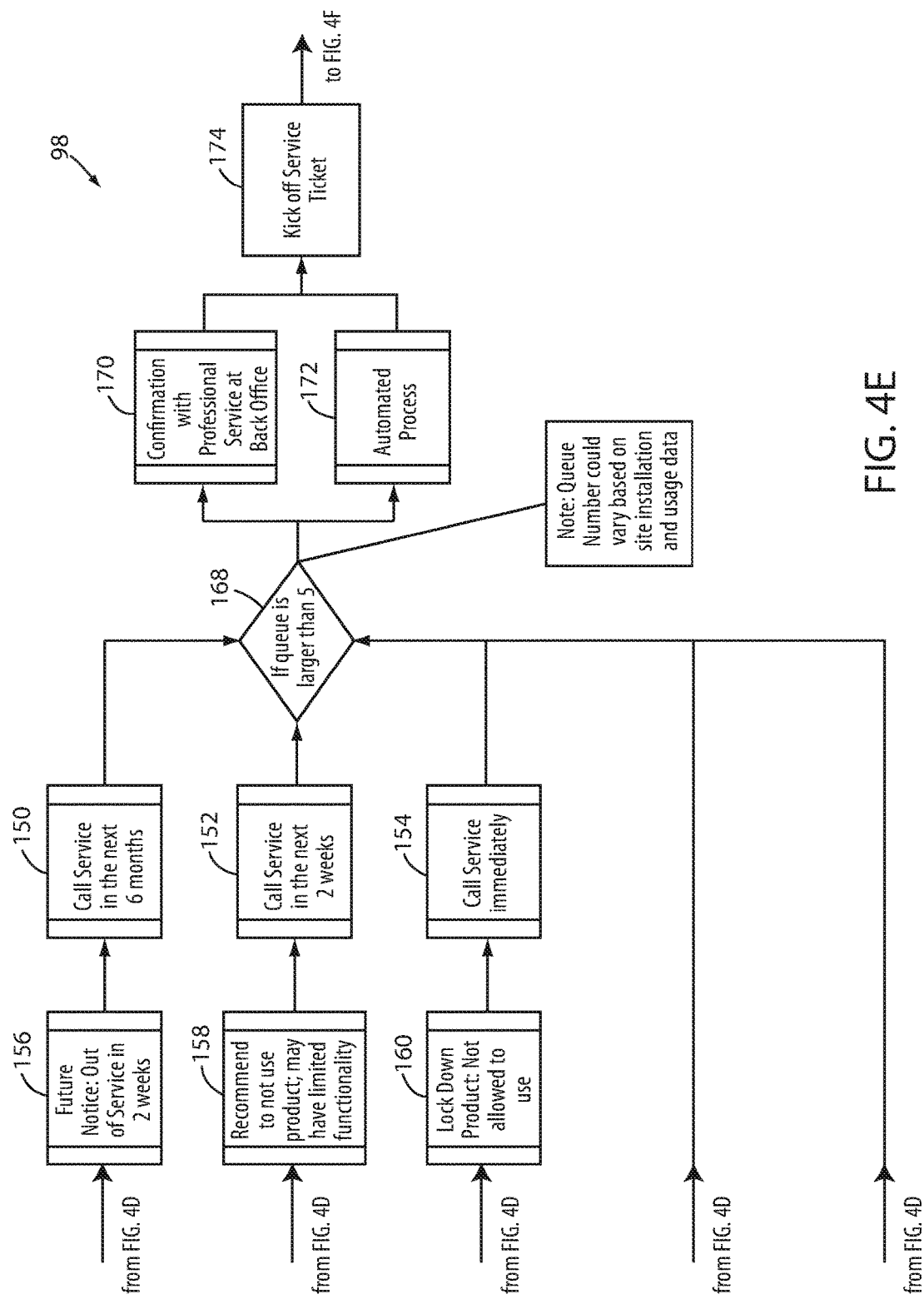
FIG. 4E is a fifth portion of the flow diagram of FIG. 4A.

Regardless of the manner in which the priority levels are assigned, the higher priority levels are indicative of a more urgent need to provide service for the corresponding patient support apparatus 20, while the lower priority levels are indicative of a less urgent need to provide service. In the example of FIG. 4E, the low priority service levels may correspond to service events for which a service call should be placed within the next six months, such as is shown in box 150. The specific amount of time can vary and, in some embodiments, is configurable by healthcare personnel via patient support apparatus server 72. Generally speaking, these low priority service levels relate to service events that are unlikely to impact any safety features or functional aspects of the patient support apparatus within the near term. Accordingly, usage of the patient support apparatus 20 can continue until the servicing event is addressed.

The medium priority levels correspond to service events that, in the embodiment of FIG. 4E, may reduce the functionality of patient support apparatus 20, but are not expected to pose a safety risk to patients or caregivers. In such cases, further use of the patient support apparatus 20 until it is serviced is not recommended due to the potential reduced functionality, but such usage may continue at the discretion of the healthcare facility personnel without compromising safety. In the illustrated embodiment, the medium priority service levels correspond to service events for which a service call should be placed within the next two weeks, such as shown in box 152 of FIG. 4E. This time can also vary and is configurable, in some embodiments, by healthcare personnel. The high priority levels correspond to service events that, in the embodiment of FIG. 4E, present safety issues, or other concerns, that should prompt a service call immediately.

Regardless of the priority level that is assigned to a service event, each detected service event is added to a service queue at steps 148*a*, *b*, or *c*. The service queue is stored in memory. In some embodiments, the memory is part of server 72, while in other embodiments the memory is remote from the healthcare facility 82. The service queue may also be stored elsewhere.

For all of the different priority levels of the service events, method 98 provides notifications to the patient support apparatus 20 and/or any and all individuals who have access to server 72, such as authorized personnel who are using computer 88 and/or smart phones 90. Examples of the types of notifications are shown in steps 150, 152, and 154. Other notifications are, of course possible.

In the illustrated embodiment, authorized personnel and/or the patient support apparatus 20 that experiences a low priority service event are notified that service should be performed on that patient support apparatus sometime within the next six months, as indicated by box 150 (FIG. 4E). Patient support apparatus 20 displays a message indicating that service should be called in a certain time period, such as six months, in some embodiments. At some point in the future, such as after a service date has been scheduled, patient support apparatus 20 switches to displaying a different notice, such as "out of service in two weeks." The specific message that is displayed, of course, varies according to the scheduled date of service.

Authorized personnel and/or the patient support apparatus 20 that experiences a medium priority service event are notified that the patient support apparatus 20 should not be used and/or that it may have limited functionality, such as shown by box 158. In some embodiments, the patient support apparatus 20 displays a message, such as "call service within two weeks," or the like, as indicated by box 152. Authorized personnel and/or the patient support apparatus 20 that experiences a high priority service event are notified that the patient support apparatus should not be used and is immediately going out of service, such as shown by box 160. In some embodiments, the patient support apparatus 20 displays a message, such as "call service immediately," or the like, as indicated by box 154. The actual notifications that are provided to the patient support apparatus 20 and authorized personnel are discussed in more detail below with respect to FIGS. 4G and 4F.

In some embodiments, the determination of the priority level of a service event is not done automatically. Instead, data about the service event is made available to one or more authorized users of servicing system 70 and the users manually determine what priority level to assign to the service event. This is indicated by box 162 of method 98

(FIG. 4D). The manual determination of the priority level of a servicing event may be done locally at the patient support apparatus 20, such as indicated by box 164, or it may be done remotely (such as via a smart phone 90 and/or computer 88), such as indicated by box 166.

Regardless of whether or not the priority level of a service event is determined locally or remotely, or automatically or manually, the service events are added to a queue and service is called for at step 168 (FIG. 4E) if the number of items in the queue exceeds a predetermined threshold. In the illustrated embodiment, the threshold is shown as being five, although it will be understood that this number may vary and that, in at least some embodiments, system 70 is configurable by authorized individuals of the healthcare facility 82 to custom tailor this threshold to whatever number they desire.

In some embodiments, prior to an actual service ticket being generated in response to the service queue reaching the corresponding threshold at step 168, method 98 seeks confirmation from an authorized professional, such as is indicated by box 170 of FIG. 4E. The authorized professional may be located at healthcare facility 82, service center 84, or at the manufacturing entity 86 that manufactured patient support apparatus 20. System 70 is configurable by the healthcare facility 82 to choose which authorized professionals to contact in carrying out the confirmation of box 170. Regardless of which authorized professional does perform this confirmation process, the actual process involves examining the service events in the queue, including any data that accompanies the service events, and deciding whether the service events and corresponding data present circumstances that indeed warrant a service ticket being generated.

As an alternative to the confirmation process of box 170, method 98 may be implemented such that the generation of service tickets occurs automatically without the need for any confirmation. This auto-generation without confirmation is illustrated by box 172 of FIG. 4E.

System 70 generates a service ticket at step 174. After generating the service ticket, method 98 proceeds to four different tasks: a product notification task 176 (FIG. 4G), a user notification task 178 (FIG. 4F), an inventory assessment task 180 (FIG. 4H), and a logistical preparation task 182 (FIG. 4H). The product notification task 176 begins with server 72 sending one or more messages to the patient support apparatuses 20 that relate to the different priority levels assigned to the service event. These messages electronically mark (i.e. designate) the patient support apparatuses 20 as being in need for service.

As one example, if a patient support apparatus 20 has experienced a low priority event, server 72 sends a notification message at step 184 to the patient support apparatus 20 that marks it as being in need of low priority service. As a result of being in this need-for-service state, controller 52 of the patient support apparatus 20 displays a message on display 58 and/or provides other aural or visual indications to the user that the patient support apparatus 20 has been designated as being in need of low priority service. The message is displayed at step 186 and indicates, for example, that "this patient support apparatus is going out of service in two weeks" or that "this patient support apparatus is scheduled for service and should not be used for a prolonged time period."

If the patient support apparatus 20 has experienced a medium priority event, server 72 sends a notification message at step 188 (FIG. 4G) to the patient support apparatus 20 that marks it as being in need of medium priority service.

As a result of being in this need-for-service state, controller 52 displays a message on display 58, such as, "this patient support apparatus is in need of service and should not be used" or "this patient support apparatus has limited functionality due to servicing needs." In some embodiments of patient support apparatus 20, controller 52 automatically limits the functionality of patient support apparatus 20 in response to the medium priority service event. Such automatic limiting of the functionality may include eliminating the controls for one or more features or functions of patient support apparatus 20. For example, if the medium priority service event relates to an error in the scale portion of the exit detection/scale system 62, controller 52 is adapted to no longer display the control or controls that enable a user to take weight readings. Alternatively, controller 52 continues to display the controls, but includes some type of indication that they are not currently available, such as, but not limited to, displaying the controls in a faded or "ghosted" fashion.

For high priority service events, server 72 sends a message at step 192 to the patient support apparatus 20 that marks it as being in need of high priority service. As a result of being in this need-for-service state, controller 52 displays a message at step 194 indicating that the patient support apparatus 20 should not be used and/or that it may be unsafe to use the patient support apparatus 20. Further, in some embodiments, the patient support apparatuses 20 that receive a high priority service message from server 72 are programmed to automatically move themselves to an unusable configuration so as to discourage and/or prevent healthcare personnel from using the patient support apparatuses 20 until they are serviced. The unusable configuration may remain until service personnel and/or server 72 sends a message to the patient support apparatus prior to service, activates a control on the patient support apparatus 20, or takes some action to terminate the unusable configuration. In some embodiments, patient support apparatus 20 automatically terminates the unusable configuration a set amount of time prior to the service date and/or service time.

The unusable configuration can vary. In some embodiments, the unusable configuration includes pivoting head section 42 to a nearly vertical orientation while also pivoting foot and/or thigh section 48 and 46 into angular positions that, in combination with the upright head section 42, make it extremely uncomfortable and/or impossible for a patient to lie or sit on the patient support apparatus 20. Once in the unusable configuration, it remains locked until terminated by a service technician, or other authorized user. In some embodiments, the locking involves terminating the operation of one or more motors.

In some embodiments, patient support apparatuses 20 are configured to automatically move to an unusable configuration only if the patient support apparatus 20 does not detect the presence of a patient on patient support apparatus 20. Detecting the presence or absence of a patient on patient support apparatus 20 can be automatically accomplished, in some embodiments, by analyzing the outputs of exit detection/scale system 62. In other embodiments, such automatic detection can be accomplished through one or more of the methods disclosed in commonly assigned U.S. patent application Ser. No. 14/928,513 filed Oct. 30, 2015, by inventors Richard Derenne et al. and entitled PERSON SUPPORT APPARATUSES WITH PATIENT MOBILITY MONITORING, the complete disclosure of which is hereby incorporated herein by reference. In still other embodiments, the detection of a patient's presence or absence can be accomplished through a video or infrared system, such as that disclosed in commonly assigned U.S. patent application Ser.

No. 14/578,630 filed Dec. 22, 2014, by inventors Richard Derenne et al. and entitled VIDEO MONITORING SYSTEM, and commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosures of both of which are incorporated herein by reference.

In some embodiments of patient support apparatuses 20, the patient support apparatuses are configured to display the messages associated with steps 186, 190, and 194 whenever a user operates, or attempts to operate, a feature or component of the patient support apparatus 20. Thus, for example, if a user attempts to lower a height of support deck 30 on a patient support apparatus that has been marked for service due to a low priority service event, controller 52 is configured to display a message, such as "out of service in two weeks" on display 58 when the user makes such an attempt. This provides a reminder to the user that the patient support apparatus 20 is due for service. Such a message is displayed automatically in some embodiments even if the user is attempting to use a control that is unrelated to the service event. For example, if the service event relates to the servicing of a motor used to drive the patient support apparatus 20 to different locations within healthcare facility 82, controller 52 displays the service message in response to the user activating controls that are unrelated to that motor, such as, but not limited to, controls used to control the exit detection/scale system 62, controls used to move the deck 30, controls used for controlling lifts 26, and/or controls used to input or edit patient information.

Further, controller 52 keeps track of the time that has passed since the service event occurred and adjusts the message based upon the passage of time. As a result, for example, if a user attempts to use the same patient support apparatus 20 a week after the low priority service event occurred, the message will indicate "out for service in one week." This message therefore gives the user an indication of how long they can still use the patient support apparatus 20 before it is scheduled to be out of service.

Controller 52 is also programmed, in some embodiments, to not only update the message displayed based upon the passage of time, but to also take one or more additional or alternative actions in response to the passage of time. For example, controller 52 is programmed in some embodiments to repetitively calculate how far away the service date is from the current date (and/or time) and to make one or more changes to the patient support apparatus 20 when the service date falls within a user-configurable time window. Such changes may include intentionally limiting the functionality of one or more components or systems of the patient support apparatus 20 in order to discourage users from selecting patient support apparatus 20 for usage as the service date approaches.

As one illustrative example, if service was scheduled to occur in one week, during the first six days after the service was scheduled, controller 52 may allow a user full access to control and use patient support apparatus. However, the day before service is scheduled (or some other time window), controller 52 may be programmed to stop providing power to a driven wheel used to propel the patient support apparatus 20 to different locations, or to reduce the power supplied to the driven wheel. This limits the functionality of the patient support apparatus 20 and makes it less desirable to use, thereby encouraging users to select a different patient support apparatus 20 for use as the service date approaches. By placing this time window close to the expected or scheduled service date, the likelihood of the patient support apparatus 20 not being used on the scheduled service day increases. This facilitates the ability of the service technician to perform the required servicing on the scheduled service day.

In some embodiments of patient support apparatuses, the time window at which the reduced functionality of patient support apparatus 20 occurs is configurable by authorized personnel of healthcare facility 82. In addition, the specific functionality that is limited is also configurable by authorized personnel of healthcare facility in some embodiments. These user configurations may be set by entering a passcode either at user interface 56 and entering the desired configuration data directly onto patient support apparatus 20 or by entering a passcode using computer 88 and/or smart phone 90 and forwarding the configuration data to server 72, which then forwards it to the appropriate patient support apparatus 20. The user interface is also adapted, in some embodiments, to allow a user to manually mark a patient support apparatus 20 as being in need of service, as being available for service (e.g. in a proper service location, not currently being used by a patient, etc.), and/or as being in a ready-for-use state (such as after servicing by a technician). Such manual changing of the service state of the patient support apparatus 20 require entering the correct passcode, in at least some embodiments, in order to prevent unauthorized changes to the servicing schedule of the patient support apparatus 20.

In some embodiments, patient support apparatuses 20 that have been marked for service only display a service message when a user attempts to assign a new patient to the patient support apparatus 20. For example, some patient support apparatuses 20 include a user interface 56 that allows a caregiver to enter the name and/or other information regarding a new patient assigned to the patient support apparatus 20. In such instances, controller 52 may be configured to display a service event message when a caregiver attempts to assign a new patient to patient support apparatus 20. This gives the caregiver notice as to whether or not it makes sense to proceed forward with the use of that particular patient support apparatus 20. If the service event is a high priority event, patient support apparatus 20 is configured in some embodiments to disallow the assigning of patient support apparatus 20 to a new patient until patient support apparatus 20 is serviced.

In still other embodiments, patient support apparatuses 20 that have been marked for service are configured to display information regarding their service event, such as a time frame for when servicing is to be expected or scheduled, in response to a user requesting such information via user interface 56. For example, user interface 56 may include an icon, menu item, or other selection feature that, when activated, displays when the next servicing date is anticipated or scheduled. The information may also include information about the service event that generated the servicing date and/or the prior history of servicing events and dates of service.

As noted, in some embodiments, the anticipated servicing of a patient support apparatus 20 is determined by patient support apparatus server 72. In such embodiments, patient support apparatus server 72 sends one or more messages to the corresponding patient support apparatus 20 indicating when the anticipated servicing will happen, and/or what information to display regarding the service event. When the service event is a high priority service event, patient support apparatus server 72 sends a command to the patient support apparatus 20 instructing the patient support apparatus 20 to move to an unusable configuration. In other embodiments, patient support apparatus 20 may be configured to determine the priority level of a service event by itself, in which case it does not receive any instructions regarding what message to display and/or whether or not to move to an unusable configuration. Further, as noted previously, the movement of the patient support apparatus 20 to an unusable configuration may be delayed until control system 50 determines that the patient support apparatus 20 is not occupied.

In some embodiments, the scheduling of a service date for a patient support apparatus 20 is accompanied by a message transmitted automatically to ADT server 74. The message tells ADT server 74 of the upcoming service date and when to no longer assign patients to this particular patient support apparatus 20.

Figure 4F:
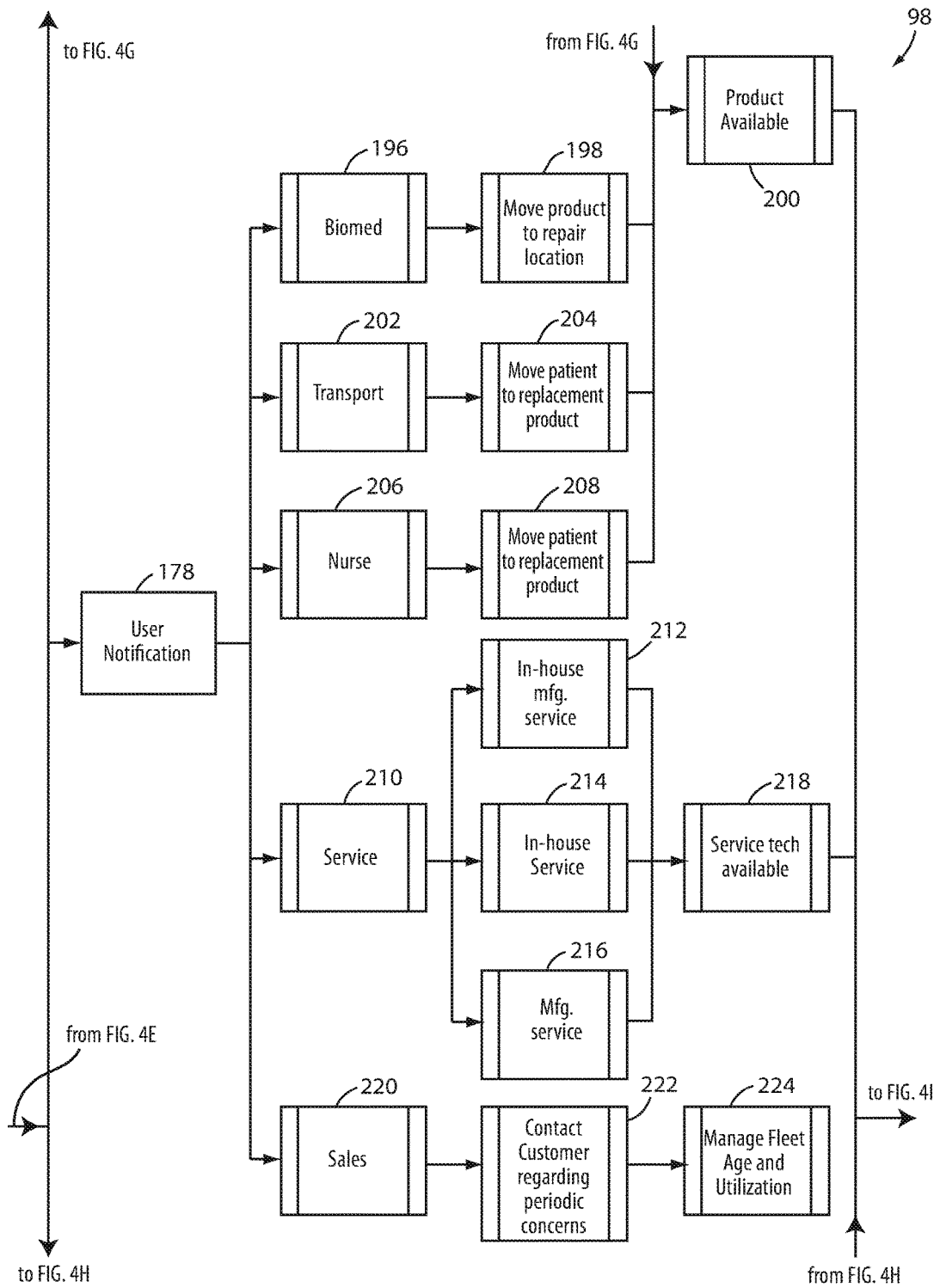
FIG. 4F is a sixth portion of the flow diagram of FIG. 4A.
Figure 4G:
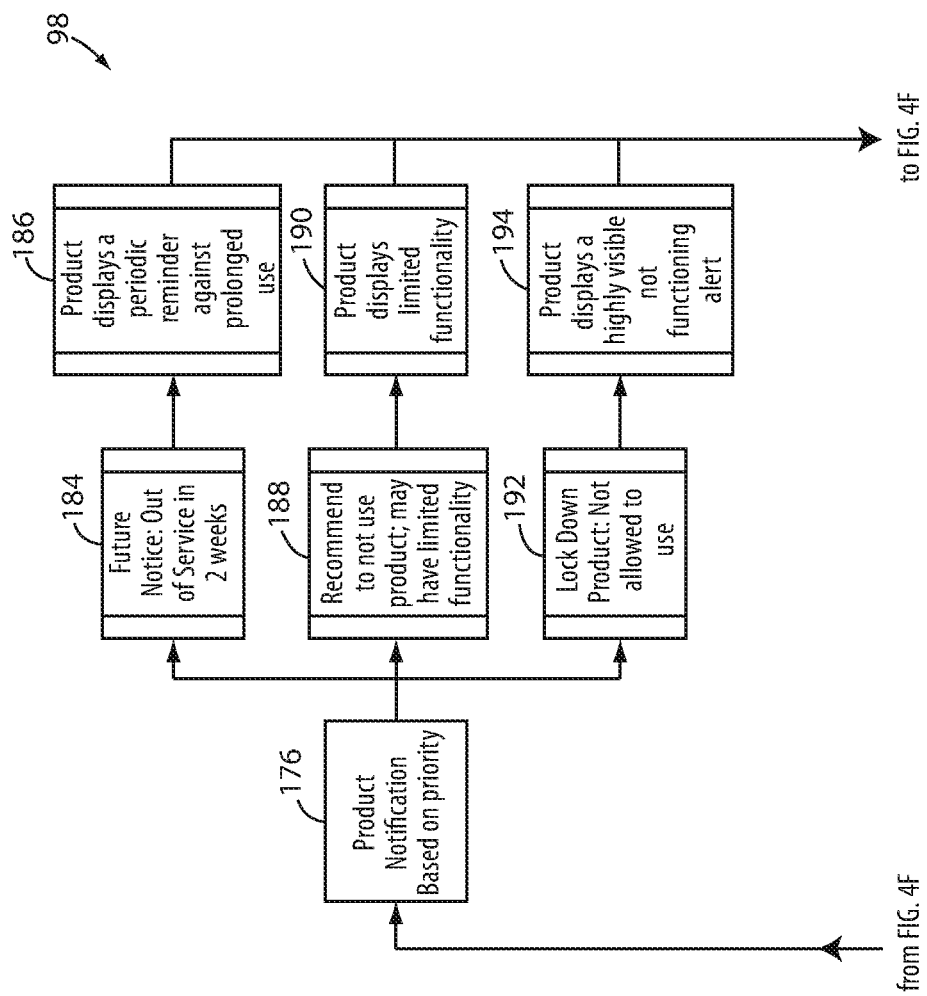
FIG. 4G is a seventh portion of the flow diagram of FIG. 4A.
Figure 4H:
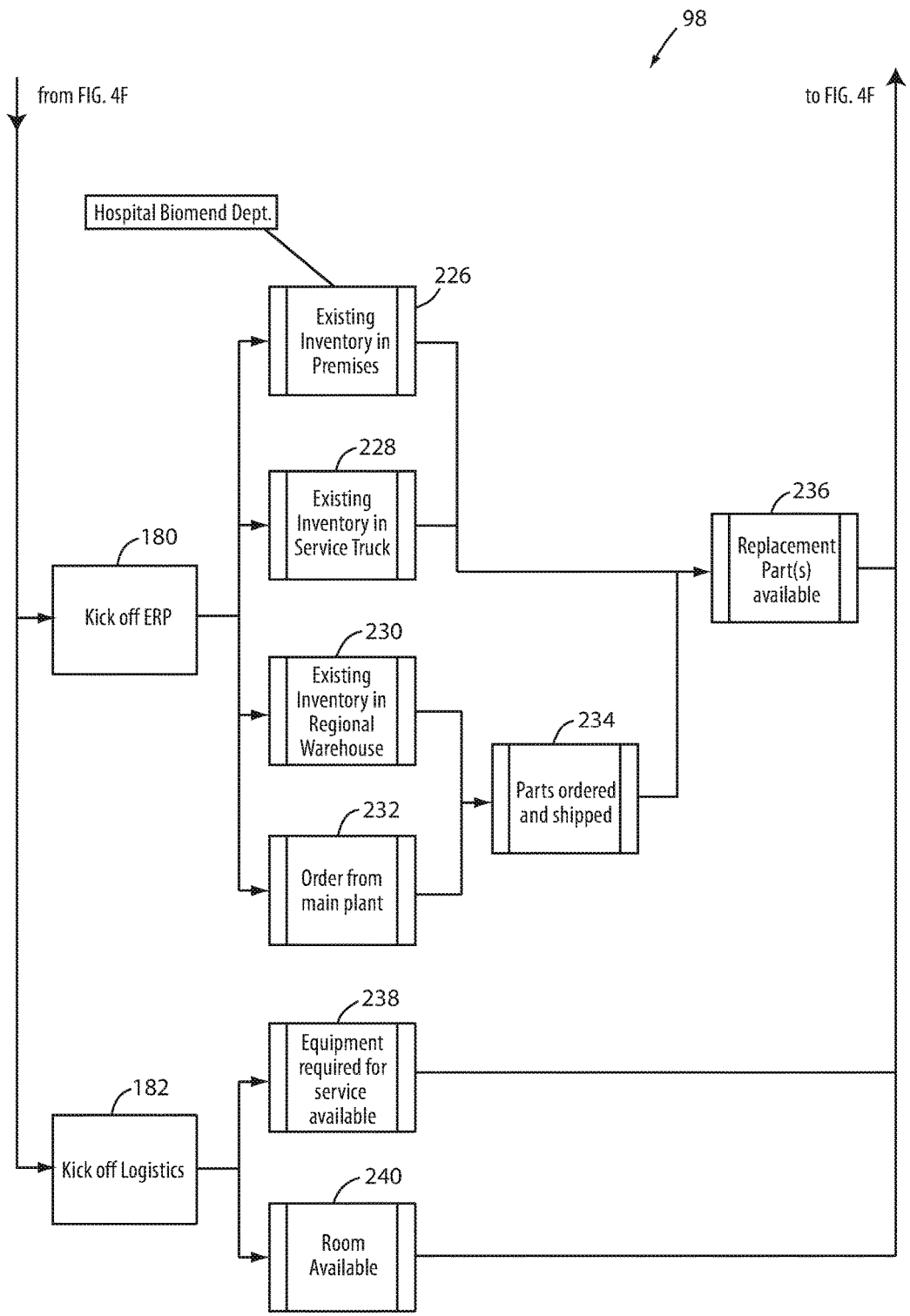
FIG. 4H is an eighth portion of the flow diagram of FIG. 4A.

In addition to the product notification task 176 illustrated in FIG. 4G, method 98 also carries out a user notification task 178 that is shown in more detail in FIG. 4F. User notification task 178 involves providing various notifications to a number of different types of individuals, such as, but not limited to, biomedical technicians or engineers, transportation personnel, caregivers (nurses or doctors), service technicians, and sales personnel. The various notifications are carried out automatically by system 70 based upon preprogrammed settings by the user. Such preprogrammed settings include the email addresses, phone numbers, and/or other contact information for each of the different individuals, or classes of individuals, who are to be contacted when carrying out notification task 178.

System 70 contacts one or more biomedical engineers or technicians at step 196 (FIG. 4F). The contact includes instructions to the biomedical engineers or technicians to move the patient support apparatus 20 experiencing the service event to a repair location, such as indicated by box 198. In some embodiments, the instruction to move the patient support apparatus 20 include a deadline for carrying out this movement that is based upon the priority level of the service event. Once such movement is carried out, the biomedical engineer or technician responds with a message (via computer 88 and/or smart phone 90) confirming that the patient support apparatus has been moved and is now available for servicing, as indicated by box 200. Alternatively, the engineer or technician may enter a required passcode through user interface 56 and mark the patient support apparatus 20 as being in an available-for-service state. Controller 52 responds to such a manual entry by forwarding a message to server 72 indicating that the patient support apparatus 20 is now available to be serviced. As yet another alternative, movement of the patient support apparatus to a repair location may be detected automatically by location server 78.

System 70 also contacts one or more transport personnel at step 202 if a patient is currently assigned to the patient support apparatus 20 experiencing a service event. This contact includes instructions to move the patient currently assigned to the marked for service patient support apparatus 20 to a different patient support apparatus 20 that has not been marked for service (or one that has been marked with a lower priority service level or one that has been scheduled for service at a later date), as indicated by box 204. System 70 make this contact in order to ensure that the patient assigned to the patient support apparatus 20 is moved to another patient support apparatus 20 before servicing is scheduled. In some embodiments, server 72 determines if a patient is currently assigned to a marked for service patient support apparatus 20 by communicating with ADT server 74. ADT server 74 stores information regarding the patients in healthcare facility 82, including what patient support apparatuses 20 each patient is assigned to. In other embodiments, other means may be used to determine if a patient is currently assigned to the patient support apparatus 20.

As an alternative to, or in addition to, step 202, system 70 is configured to contact one or more caregivers (such as nurses) assigned to the patient currently occupying the marked for service patient support apparatus 20 at step 206 of FIG. 4F. System 70 performs this step in addition to step 202 in some embodiments in order to ensure that either a transport person or a caregiver moves the patient to a different patient support apparatus. In other embodiments, healthcare facility 82 may not include personnel dedicated to transporting patients, so step 202 may be omitted and replaced with step 206. In still other embodiments, step 206 may be omitted and the transfer of a patient to a different patient support apparatus 20 may be accomplished via step 202. In any of these embodiments, the result is the transfer of the patient to a different patient support apparatus 20 that is not being scheduled for service at the same time as the one currently assigned to the patient, as indicated by boxes 204 and 208.

As part of user notification task 178, system 70 also contacts one or more service personnel at step 210 (FIG. 4F). In some embodiments, the contacted service personnel include one or more representatives of manufacturing entity 86 who work on-site at healthcare facility 82 or who otherwise frequent healthcare facility 82, as indicated by box 212. Alternatively, or additionally, system 70 makes contact with one or more in-house service personnel who work directly for healthcare facility 82, as indicated by box 214. At yet another alternative or addition, system 70 makes contact with one or more personnel associated with manufacturing entity 86 who do not work on site at healthcare facility 82, or who otherwise are not associated with healthcare facility 82 and are located remotely therefrom, as indicated by box 216.

After notification of the service personnel at step 210, system 70 proceeds to determine, or receive, availability information regarding the service personnel contacted during step 210. In some cases, the contacted personnel input their availability into system 70 (via computers 88, 94 or via phones 90, 92), while in other cases such information is already made available to system 70. In the latter case, server 72 may be in communication with a computer calendar of the personnel that they maintain on their computers 88, 94 and/or phone 90, 92. Regardless of how the availability of the contacted service personnel is determined, method 98 proceeds to determine and identify one or more time slots in which those service personnel are available for carrying out the servicing, as indicated by box 218.

As part of user notification task 178, system 70 may also contact one or more sales personnel at step 220 (FIG. 4F). Such sales personnel are associated with manufacturing entity 86 and inform the sales personnel of servicing issues that have arisen. This enables the sales personnel to make appropriate contact with the client (healthcare facility 82) in light of the servicing events and/or sales history, as indicated by box 222. Further, such contact helps the sale agent to assist the healthcare facility 82 with the managements and utilization of the fleet of patient support apparatuses 20 used by the healthcare facility 82, as indicated by box 224.

In addition to the product notification and service personnel notification tasks 176 and 178 illustrated in FIGS. 4G and 4F, method 98 also carries out an inventory assessment task 180 that is shown in more detail in FIG. 4H. Inventory assessment task 180 involves determining if one or more replacement parts are needed for carrying out the planned servicing. Additionally, assessment task 180 determines if any needed parts are currently available at healthcare facility 82 and/or service center 84 and, if not, generates an order for the needed parts.

More specifically, task 180 includes an on-premise inventory assessment step 226 in which system 70 checks to see if the needed part(s) are currently available in an inventory stored on the premises of healthcare facility 82. This is accomplished by communicating with inventory control server 76. In addition, task 180 includes a service truck inventory assessment step 228 in which system 70 checks to see if the needed part(s) are currently available on a service truck that is scheduled to make a delivery at healthcare facility 82. If the part(s) are determined to be available at either step 226 or 228, system 70 indicates the availability of the part(s) at step 236. If the parts are not determined to be available at steps 226 or 228, system 70 executes a warehouse inventory assessment step 230 in which system 70 checks to see if the needed part(s) are currently available in a warehouse. If they are available, the needed part(s) are ordered at step 234 from the warehouse, which may be located at the same location as service center 84, or it may be located elsewhere. The arrival of the ordered parts is noted at step 236.

If the needed part(s) are not currently available on-premise, on a service truck, or at a warehouse, system 70 orders the needed part(s) at step 232 from the manufacturer, such as manufacturing entity 86. The ordered parts are shipped at step 234 and system 70 marks the arrival of the ordered parts at healthcare facility 82 at step 236 and/or the expected arrival date.

In addition to the product notification, service personnel notification, and inventory assessment tasks 176, 178, and 180 illustrated in FIGS. 4G, 4F, and 4H, method 98 also carries out a logistical preparation task 182 (FIG. 4H). Logistical preparation task 182 includes an equipment assessment step 238 in which system 70 determines when the equipment needed to perform the servicing of patient support apparatus 20 (if needed) is, or will be, available at healthcare facility 82 and/or service center 84. If it is not currently available, system 70 orders the necessary equipment or automatically contacts appropriate personnel who can order the necessary equipment. Logistical preparation task 182 also includes a room assessment step 240 in which system 70 determines when a designated room for servicing patient support apparatus 20 will be available.

Figure 4I:
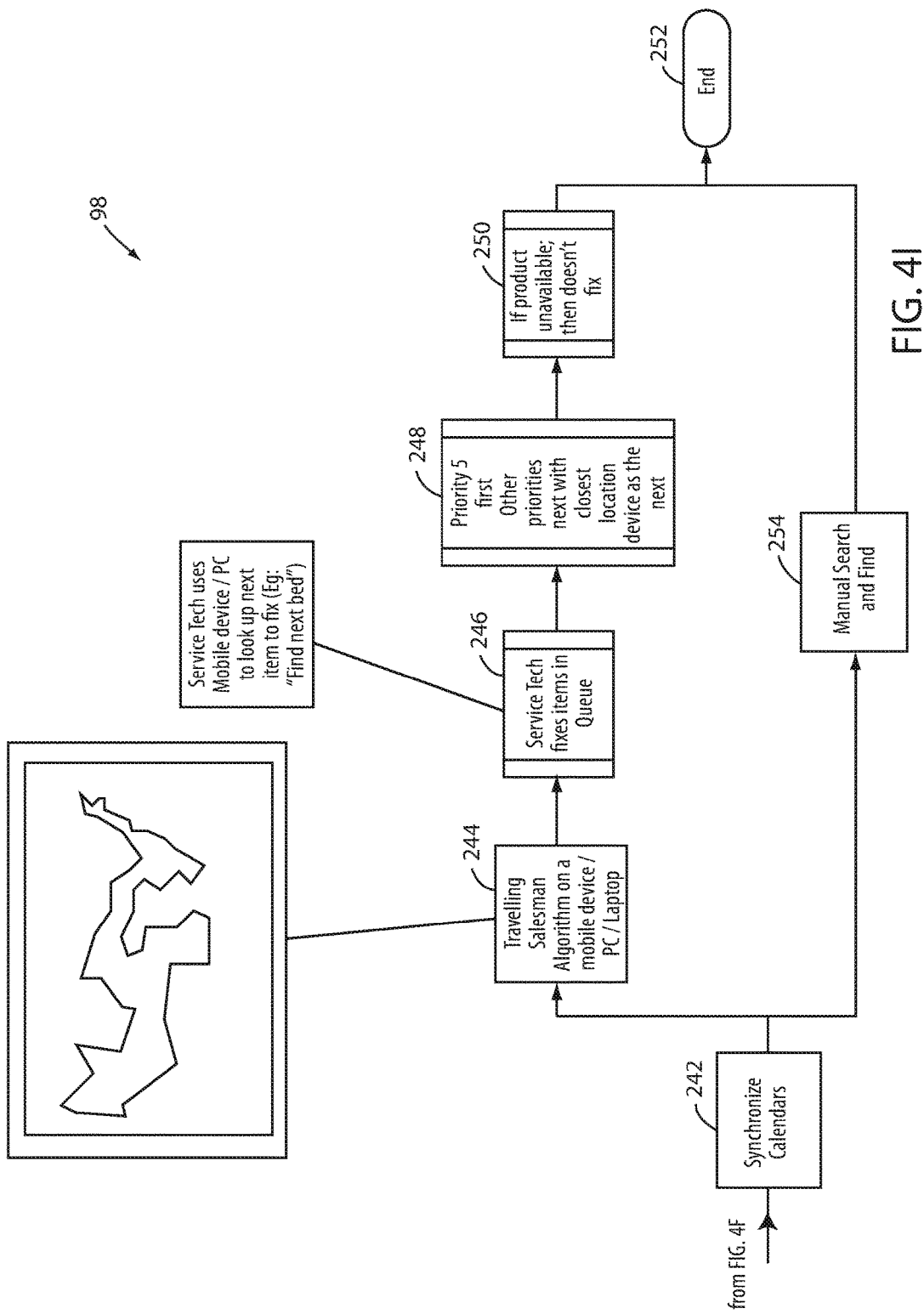
FIG. 4I is a ninth portion of the flow diagram of FIG. 4A.

The results of tasks 176, 178, 180, and 182 all feed into a synchronization step 242 (FIG. 4I). At synchronization step 242, system 70 determines times when the product notification task 176, user notification task 178, inventory assessment task 180, and logistical preparation task 182 overlap with each other. That is, system 70 identifies the dates and/or times when the patient support apparatus 20 indicates it will be out of service (as part of task 176), identifies the dates and/or times when the patient support apparatus 20 and the appropriate service personnel will be available (as part of task 178), identifies the dates and/or times when the required part(s) (if any) will be available, and also identifies the dates and/or times when the room and/or equipment used for servicing patient support apparatus 20 are or will be available. Based on these four sets of identified times, system 70 identifies the subset of times that are common to all four tasks and uses those common times to schedule servicing for the patient support apparatus 20 at step 242. All parties and/or subsystems that are associated with the servicing are then notified of the scheduled service date (e.g. the service technician, the patient support apparatus 20, the caregivers, the transport personnel, any room reservation service or program, etc.). If the scheduled service date differs from the service date that was previously displayed on one or more patient support apparatuses 20, the patient support apparatuses 20 adjust their messages and/or actions to correspond to the newly computed service date.

In some embodiments, synchronization step 242 also takes into account data regarding the schedule of any patient that is currently assigned to a patient support apparatus 20 that has been marked for service. Such scheduling data may come from ADT server 74 or from other sources. The scheduling data provides information about the location of the patient and the scheduling of any procedures or tasks associated with the patient. For example, the patient may be scheduled to have an X-ray taken at a certain time of day, or to be transferred to a different room for some other type of medical procedure. System 70 uses this data in some embodiments when carrying out synchronization step 242. That is, system 70 also takes into account when determining a service date those times when the patient support apparatus 20 may be unoccupied by the patient due to the patient having a procedure performed at a different location within healthcare facility 82 and/or due to the patient being discharged from the healthcare facility.

Steps 244 through 252 of FIG. 4I are performed by system 70 and relate to the determination of which order service calls are to be carried out by a service technician. At step 244, system 70 uses a conventional traveling salesman algorithm to determine the order in which he or she should provide service to the different healthcare facilities 82 that he or she is responsible for visiting. This algorithm takes into account the current location of all of the healthcare facilities 82 assigned to that particular service technician that have at least the threshold number of patient support apparatuses 20 in their service queue. In general, the traveling salesman algorithm computes an order of performing the patient support apparatus servicing that reduces and/or minimizes the amount of traveling that the service technician needs to undertake in order to provide service to the various healthcare facilities 82. After this algorithm is completed, messages may be sent to each of the patient support apparatuses 20 scheduled to be serviced, and/or to server 72, that provide a more accurate time window for the expected service based upon the results of the traveling salesman calculation.

Once the service technician arrives at a particular healthcare facility 82, the service technician proceeds to step 246 where he or she looks up the patient support apparatuses 20 in the service queue to determine which patient support apparatuses 20 need servicing while visiting that particular healthcare facility. This step may be accomplished by the service technician using his or her smart phone or computer and accessing information stored on server 72, or another component of system 70. The smart phone or table may include an app on it that includes a "find next patient support apparatus" function that automatically identifies to the salesperson the next patient support apparatus 20 that is to be serviced by that technician.

When presenting the queue of patient support apparatuses 20 to the service technician, system 70 automatically displays the queue in the order of the priority levels, as indicated at step 248 (FIG. 4I). The patient support apparatuses 20 having the highest priority are listed first and the lowest priority listed last. Additionally, if more than one patient support apparatus 20 has the same priority level, system 70 orders the patient support apparatuses 20 based on those that are nearest to the technician so that he or she can provide service first to the closest patient support apparatus 20. This ordering may be accomplished by using the location features of the smart phone (e.g. cellular triangulation and/or WiFi triangulation) or other mobile device that is carried by the service technician, and which communicates with server 72 and/or computer network 68. The location of the service technician is then compared to the location of the various patient support apparatuses 20, as determined in any of the manners previously described. The queue may alternatively be ordered based upon the type of service, location, and/or manual preferences of the technician. Authorized personnel can also add to the queue manually at any time, including after a service technician has arrived at the medical facility and commenced service work.

If, for some reason, a particular patient support apparatus 20 is unavailable at the time the service technician is on-site, service for that particular patient support apparatus 20 is skipped and remains on the queue for servicing in the future, as indicated by box 250 of FIG. 4I. After all of the available patient support apparatuses 20 have been serviced by the service technician, those patient support apparatuses 20 are marked as being ready-for-use, either manually by the service technician or automatically by system 70. Method 98 then comes to an end at step 252.

In some embodiments, as indicated by step 254 of FIG. 4I, system 70 does not provide an order for servicing the patient support apparatuses 20 at a particular healthcare facility 82. Instead, the service technician manually searches for and finds the patient support apparatuses 20 that need servicing and services them in the order that he or she chooses. In such embodiments, after all of the available patient support apparatuses 20 are serviced by the technician, method 98 terminates at step 252.

Still further, in some embodiments, system 70 may modify the suggested order in which patient support apparatuses 20 are to be serviced based upon the schedule of any patients that are assigned to those patient support apparatuses 20. That is, in some instances, a healthcare facility 82 may choose to continue to use a patient support apparatus 20 that has been scheduled for service up to and through the day at which the service has been scheduled, or the patient support apparatus 20 that has been scheduled for service may otherwise be occupied on the day of the scheduled service. In such instances, there may be an opportunity for the service technician to service the patient support apparatus 20 based upon the schedule of the patient. Thus, as mentioned above, system 70 may consult ADT server 74 and determine if the patient is scheduled to be away from the patient support apparatus 20 at any point while the service technician is on site. If so, system 70 notes such times to the service technician so that the service technician is provided with the opportunity to service patient support apparatuses 20 when they are unoccupied. Alternatively, or additionally, system 70 may request ADT server 74 assign a substitute patient support apparatus 20 to a patient so that the patient support apparatus 20 needing service can be serviced without being assigned to a patient.

It will be understood that, although a large number of specific steps have been described as part of method 98, any one or more of the specific steps described herein may be omitted in different embodiments. For example, in some embodiments, method 98 does not undertake all of the user notification steps illustrated in FIG. 4F (e.g. steps 196, 202, 206, 210, and 220), but instead only executes a subset of these notification tasks. In other embodiments, one or more of the tasks 176, 178, 180, and/or 182 are omitted, reduced, or supplemented. In still other embodiments, one or more other modifications may be made.

Further, although most of the description of method 98 provided herein has described server 72 as performing the bulk of the steps of method 98, it will be understood that any one or more of the tasks described herein as being performed by server 72 may be performed elsewhere, such as, but not limited to, by one or more other servers in healthcare facility 82, onboard the patient support apparatuses 20, on one or more of the computers 88 or smart phones 90 used in the healthcare facility 82, or at any of the computers or servers located outside of the healthcare facility 82 (e.g. computers 94, server 96, and/or smart phones 92).

It will also be understood that, although system 70 and method 98 have been described herein as being applied specifically to patient support apparatuses 20, they may be modified and applied to any type of medical devices or equipment within a healthcare facility. Indeed, in some embodiments, system 70 and method 98 are modified to operate in conjunction with the equipment management system disclosed in commonly assigned U.S. patent application Ser. No. 62/361,221 filed Jul. 12, 2016, by inventor David Becker and entitled EQUIPMENT MANAGEMENT SYSTEM, the complete disclosure of which is incorporated herein by reference. When so modified, patient support apparatuses 20 communicate with a cloud-based platform that detects and/or monitors service events and performs the scheduling and coordination tasks described herein.

In some embodiments, the movement of the patient support apparatuses 20 to and from their servicing locations is carried out automatically by way of self-driving patient support apparatuses 20, such as those disclosed in commonly assigned U.S. patent application Ser. No. 13/795,193 filed Mar. 12, 2013, by inventors Richard Derenne et al. and entitled POWERED PATIENT SUPPORT APPARATUS, the complete disclosure of which is incorporated herein by reference.

Figure 5:
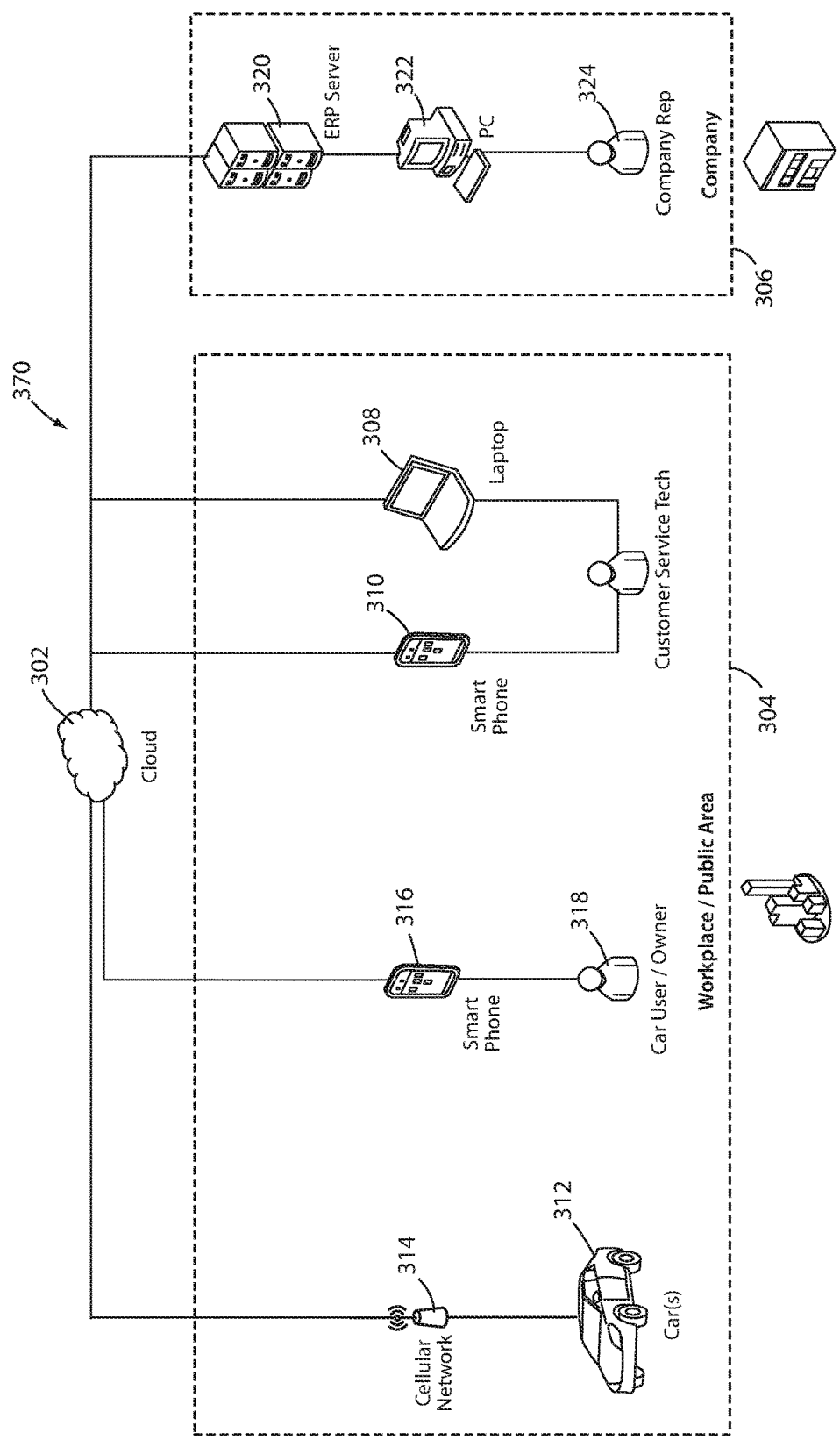
FIG. 5 is a diagram of an automotive servicing system according to another embodiment of the present disclosure.

FIG. 5 illustrates an alternative servicing system 370 that is adapted to be used for monitoring, processing, scheduling, and carrying out the servicing of a fleet of automobiles. System 370 includes a cloud-based platform or server 302 that communicates with both a workplace 304 and an automotive company 306. Workplace 304 refers to a place where servicing of automobiles takes place. Workplace 304 includes one or more computers 308 and one or more smart phones 310, both of which are used by one or more service technicians associated with workplace 304. Smart phones 310 and computers 308 are in communication with server 302 via an Internet connection. Server 302 also communicates with one or more automobiles 312 via a cellular network 314. Still further, server 302 communicates with one or more automobile owners or users 318 via the smart phones 316 of the automobile owners.

Automotive company 306 may be an automobile manufacturer and/or an automotive parts manufacturer or supplier. Automotive company 306 includes an Enterprise Resource Planning (ERP) server 320, one or more computers 322 in communication with ERP server 320, and one or more automotive company personnel 324.

In operation, system 370 monitors each of the automobiles 312 within the fleet of automobiles that are part of system 370. In some embodiments, the fleet may be a rental car fleet, while in other embodiments the fleet may be comprised of another set of automobiles 312. The automobiles report service events that they themselves detect to server 302 via cellular network 314, or they report data detected by on-board sensors that is processed by server 302 to detect service events (or a combination of both). Once a service event is detected, server 302 proceeds in the same manner as discussed above with respect to system 70. In overview, server 302 coordinates the scheduling of service for the automobile 312 with the owner or user 318 and the service technicians associated with workplace 304. Server 302 also checks part inventories and/or logistical needs to ensure that parts and/or equipment are available for the required service. The checking of the parts and logistical supplies is performed both with respect to parts and equipment that are maintained at workplace 304 and at automotive company 306. Once the calendars of the service technicians and owners/users are examined to find common dates that are available for performing the servicing, system 70 selects a commonly available date for scheduling the service that also allows the necessary parts and/or equipment to be available. Depending upon the service priority level and/or the time until the scheduled service date, reduced functionality of the automobile 312 may be implemented by system 370. Once the service day arrives, service is performed and the automobiles are marked as being ready for use (i.e. not in need of service).

In some embodiments, the user and/or owner receives a warning phone call, text, email, or the like. Further, arrangements for loaners may be made and/or substitute cars may be transport to replace the cars needing service. In some cases, the authentication of the substitute car is activated for the user automatically.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a frame;
a support surface supported on the frame and adapted to support a patient thereon;
a display; and
a controller adapted to receive data indicating that the patient support apparatus has been scheduled for service and to provide an indication on the display that the patient support apparatus has been scheduled for service, the service relating to maintenance work for a component of the patient support apparatus, wherein the controller is further adapted to limit a function of the patient support apparatus based upon a comparison of a current date to a date on which the patient support apparatus has been scheduled for service.

2. The patient support apparatus of claim 1 further including a user interface wherein the controller is adapted to receive the data indicating that the patient support apparatus has been scheduled for service from the user interface.

3. The patient support apparatus of claim 1 further including a transceiver adapted to communicate with a local area network wherein the controller is adapted to receive the data indicating that the patient support apparatus has been scheduled for service from the transceiver.

4. The patient support apparatus of claim 1 further including a user interface having a plurality of controls adapted to control a plurality of functions of the patient support apparatus, wherein the controller displays the indication in response to a user activating one or more of the controls.

5. The patient support apparatus of claim 1 wherein the indication includes data regarding the date for which the patient support apparatus has been scheduled for service.

6. The patient support apparatus of claim 1 wherein the controller is further adapted to receive a priority level associated with the scheduled service and change the indication based upon the priority level.

7. A patient support apparatus comprising:
a frame;
a user interface having a control adapted to be activated by a user;
a support surface supported on the frame; and
a controller adapted to control a function of the patient support apparatus in response to the user activating the control, the controller further adapted to provide notification to the user of a service event relating to maintenance work for a component of the patient support apparatus, the controller further adapted to limit functionality of the patient support apparatus based upon a severity of the service event, the controller limiting functionality of the patient support apparatus in at least one of the following manners: (a) not carrying out the function in response to the user activating the control; or (b) partially carrying out the function in response to the user activating the control.

8. The patient support apparatus of claim 7 wherein the severity of the service event is determined by a remote device in communication with the controller.

9. The patient support apparatus of claim 7 wherein the severity of the service event is categorized according to at least three levels, a first one of the three levels corresponding to a high priority level, a second one of the three levels corresponding to a medium priority level, and a third one of the three levels corresponding to a low priority level.

10. The patient support apparatus of claim 9 further including a user interface adapted to allow a user to set the priority level of the service event.

11. The patient support apparatus of claim 9 wherein the controller provides notification to a user but does not limit functionality of the patient support apparatus if the service event corresponds to a low priority level; the controller limits functionality of the patient support apparatus in manner (b) if the service event corresponds to a medium priority level; and the controller limits functionality of the patient support apparatus in manner (a) if the service event corresponds to a high priority level.

12. The patient support apparatus of claim 7 wherein the function of the patient support apparatus does not use the component of the patient support apparatus to which the service event relates.

13. The patient support apparatus of claim 7 wherein the controller communicates usage information to a remote device and the remote device uses the usage information to detect the service event.

14. The patient support apparatus of claim 7 wherein the service event is at least one of the following: a scheduling of a time at which maintenance work on the component is to be performed by a service person; and an arrival of a time window associated with a scheduled service time for performing maintenance work on the component.

15. The patient support apparatus of claim 7 wherein the component is a motor on the patient support apparatus, the function is moving a portion of the patient support apparatus via the motor, and the controller limits functionality of the patient support apparatus by not activating the motor in response to the user activating the control.

16. The patient support apparatus of claim 7 wherein the component is a load cell and the controller prevents a weight measurement from being taken, and prevents an exit detection system from being armed.

17. The patient support apparatus of claim 7 wherein the user interface is further adapted to enable a user to change a state of the patient support apparatus from an in-use state to a ready-for-service state.

18. The patient support apparatus of claim 17 wherein the controller is adapted to send a message to a remote device indicating the current state of the patient support apparatus.

19. A patient support apparatus comprising:
- a frame;
- a support surface supported on the frame;
- a memory for storing marking data, the marking data indicating whether the patient support apparatus has been marked for use or marked for service;
- a first control for carrying out a first function of the patient support apparatus, the first function not involving reading the marking data or storing the marking data in the memory; and
- a controller adapted to detect when the first control is activated by a user and, in response to such activation, examine the marking data to determine whether the patient support apparatus has been marked for use or marked for service, and if the patient support apparatus has been marked for use, to respond to the activation of the first control in a first manner, and if the patient support apparatus has been marked for service, to respond to the activation of the first control in second manner, the second manner being different from the first manner.

20. The patient support apparatus of claim 19 wherein the first manner includes carrying out the first function of the patient support apparatus without a predetermined limit, and the second manner includes at least one of the following: carrying out the first function of the patient support apparatus with the predetermined limit, and not carrying out the first function of the patient support apparatus.

21. The patient support apparatus of claim 19 wherein the first manner includes carrying out the first function of the patient support apparatus and the second manner includes carrying out the first function of the patient support apparatus and changing how the controller reacts to a subsequent activation of a second control for carrying out a second function of the patient support apparatus.

22. The patient support apparatus of claim 19 wherein the patient support apparatus includes a transceiver for receiving the marking data from a remote device.

23. The patient support apparatus of claim 19 further comprising a second control adapted to allow the user to input the marking data.

24. The patient support apparatus of claim 19 wherein the second manner varies based upon a comparison of a current time and date with a scheduled service time and date, and the second manner includes not carrying out the first function if the current time and date fall within a time window associated with the scheduled service time and date.

25. The patient support apparatus of claim 1 wherein the maintenance work for the component of the patient support apparatus includes at least one of repairing the component, replacing the component, lubricating the component, or calibrating the component.

* * * * *